US008649849B2

(12) United States Patent
Liu et al.

(10) Patent No.: US 8,649,849 B2
(45) Date of Patent: Feb. 11, 2014

(54) OPTICAL METHODS TO INTRAOPERATIVELY DETECT POSITIVE PROSTATE AND KIDNEY CANCER MARGINS

(75) Inventors: Hanli Liu, Arlington, TX (US); Jeffrey A. Cadeddu, Dallas, TX (US); Disha L. Peswani, Kalamazoo, MI (US)

(73) Assignee: Board of Regents, The University of Texas System, Austin, TX (US)

( * ) Notice: Subject to any disclaimer, the term of this patent is extended or adjusted under 35 U.S.C. 154(b) by 462 days.

(21) Appl. No.: 12/600,975

(22) PCT Filed: May 21, 2008

(86) PCT No.: PCT/US2008/064429
§ 371 (c)(1),
(2), (4) Date: Apr. 14, 2010

(87) PCT Pub. No.: WO2008/144760
PCT Pub. Date: Nov. 27, 2008

(65) Prior Publication Data
US 2010/0198080 A1    Aug. 5, 2010

Related U.S. Application Data

(60) Provisional application No. 60/939,239, filed on May 21, 2007.

(51) Int. Cl.
*A61B 6/00* (2006.01)
(52) U.S. Cl.
USPC .......................................... 600/476; 356/629
(58) Field of Classification Search
USPC ................... 600/476–478, 109, 160
See application file for complete search history.

(56) References Cited

U.S. PATENT DOCUMENTS

| | | | |
|---|---|---|---|
| 6,826,424 B1* | 11/2004 | Zeng et al. | 600/476 |
| 6,912,412 B2* | 6/2005 | Georgakoudi et al. | 600/310 |
| 6,975,899 B2* | 12/2005 | Faupel et al. | 600/476 |
| 7,280,866 B1* | 10/2007 | McIntosh et al. | 600/475 |
| 7,751,039 B2* | 7/2010 | Ramanujam et al. | 356/244 |
| 2004/0006276 A1* | 1/2004 | Demos et al. | 600/476 |
| 2005/0203419 A1* | 9/2005 | Ramanujam et al. | 600/473 |
| 2011/0319759 A1* | 12/2011 | Liu et al. | 600/439 |

FOREIGN PATENT DOCUMENTS

WO    2005052558    6/2005

OTHER PUBLICATIONS

X Shao, W Zheng, Z Huang. Polarized near-infrared autofluorescence imaging combined with near-infrared diffuse reflectance imaging for improving colonic cancer detection. Optics Express 18(23): Nov. 2010.*
JW Tunnell, AE Desjardins, L Glaindo, I Georgakoudi, SA McGee, J Mirkovic, MG Mueller, J Nazemi, FT Nguyen, A Wax, Q Zhang, RR Dasari, MS Feld. Instrumentation for multi-modal spectroscopic diagnosis of epithelial dysplasia. Technology in Cancer Research & Treatment 2(6): Dec. 2003.*

* cited by examiner

*Primary Examiner* — Unsu Jung
*Assistant Examiner* — Amanda Lauritzen Moher
(74) *Attorney, Agent, or Firm* — Winstead PC

(57) ABSTRACT

The present invention includes using optical spectroscopy as an innovative technique for ex-vivo demonstration of renal and prostate tumors. The apparatus and methods disclosed herein demonstrate the ability of optical spectroscopy to reliably differentiate tumor from normal tissue in renal specimens.

14 Claims, 30 Drawing Sheets

(a)

(b)

(a)

(b)

(c)

(a)

(b)

(a) (b)

OPTICAL METHODS TO INTRAOPERATIVELY DETECT POSITIVE PROSTATE AND KIDNEY CANCER MARGINS

BACKGROUND OF THE INVENTION

Without limiting the scope of the invention, its background is described in connection with the field of in vivo cancer detection, more particularly, optical methods to intra-operatively detect cancer margins in prostate and kidney cancers.

Clinically localized prostate cancer is generally treated with either radiation therapy or surgery. Surgical treatment is currently undergoing a significant revolution; that is laparoscopic radical prostatectomy (LRP). This procedure permits complete removal of the prostate and seminal vesicles while minimizing pain and recovery. However, the laparoscopic approach greatly limits tactile sensation during the procedure. This is particularly true with robot-assisted LRP where no tactile feedback is available forcing the surgeon to rely solely on visual cues.

Kidney cancer is increasingly detected at very early stages due to the wide spread use of axial imaging for a variety of complaints. Associated with this stage migration is an increase in the incidence of benign histology associated with such tumors. In fact, 15-20% of renal tumors measuring less than 4 cm are benign. However, traditional diagnostic needle biopsy of small renal masses is not commonly performed due to its consistent and clinically unacceptable false negative rate. As such, nephron-sparing surgery (i.e. partial nephrectomy) is a preferred management technique for most small tumors. The advantage of this approach is that it preserves kidney function, especially in those cases of benign disease. However, both open and laparoscopic partial nephrectomies usually require renal ischemia to excise the tumors safely creating a unique, technically challenging procedure with significant time pressures to limit the renal insult. Of course, complete excision with a negative margin is required to minimize the risk of tumor recurrence but unfortunately, the surgeon cannot evaluate the surgical specimen until the procedure is completed and specimen extracted. Although intraoperative frozen section pathologic analysis of a few select tissue fragments from the resected specimen or renal parenchyma can be obtained, it is time consuming risking renal ischemic injury and costly. Furthermore, concrete conclusions based on such samples are unreliable, as they do not reflect the entire surgical margin status.

Kidney tumors are intraparenchymal tumors that are commonly malignant. For early clinically localized kidney tumors, it is not possible to reliably confirm benign versus malignant disease or identify the deep parenchymal tumor margin during surgery. Prostate cancer, on the other hand, is an intraparenchymal tumor that is commonly multifocal. For early clinically localized prostate cancer, it is also not possible to visually identify the tumor during surgery, either within the prostate or at its capsular margin. Because of this, it would be highly desirable to develop an optical spectroscopic approach that will allow the surgeon in real time percutaneously confirm a cancer or benign diagnosis, and, during surgical excision of confirmed malignancies, to detect renal carcinoma at the surgical margin during resection.

In recent years, varieties of optical spectroscopy techniques have been developed for detection and diagnosis of different kinds of cancers. However, most of these techniques mainly target luminal malignancies, such as cervical, colon, and esophageal cancers. For example, U.S. Pat. No. 6,912,412 discloses a plurality of spectroscopic systems and methods to measure characteristics of tissue useful in the diagnosis of disease. In the '412 patent, a combination of fluorescence, reflectance and light scattered spectra can be measured and processed to provide biochemical, architectural and morphological state of tissue. The methods and systems can be used particularly in the early detection of carcinoma within tissue in vivo and in vitro.

Another example is shown is U.S. Pat. No. 7,309,867 issued to Costa et al. Costa provides methods for determining the probability that a given region of a tissue sample contains tissue of a given category, such as CIN 1 (cervical intraepithelial neoplasia, grade 1), CIN 2/3 (cervical intraepithelial neoplasia grades 2 and/or 3), normal squamous, normal columnar, and metaplasia. The '867 patent provides increased diagnostic accuracy by combining a plurality of statistical classification techniques. Furthermore, it mentioned combining one or more statistical techniques with one or more non-statistical classification techniques.

One can also see an example shown in U.S. Pat. No. 7,282,723. The '723 patent discloses methods for processing tissue-derived spectral data for use in a tissue classification algorithm. Methods include application of spectral and/or image masks for automatically separating ambiguous or unclassifiable spectral data from valid spectral data. The '723 patent improves the accuracy of tissue classification, in part, by properly identifying and accounting for spectral data from tissue regions that are affected by an obstruction and/or regions that lie outside a diagnostic zone of interest.

Yet another example can be found in U.S. Pat. No. 7,248,909 issued to Lee et al. Lee shows device and method utilizes a broadband diffuse optical spectroscopy (DOS) system to dynamically calculate the concentrations of multiple chromophores in vivo using a non-invasive probe. The device and method permit dynamic monitoring of multiple in vivo tissue chromophores non-invasively with sensitivities necessary for effective therapeutic monitoring. The device includes a probe containing first and second source optical fibers as well as first and second detector optical fibers. The probe is placed adjacent to a sample of interest and detects reflected light which is passed to a proximally located detector and spectrometer. The concentrations of multiple chromophores are determined in real time. In an example, the multiple tissue chromophores include at least two of methemoglobin (MetHb), deoxyhemoglobin (Hb-R), oxyhemoglobin (Hb-$O_2$), water ($H_2O$), and methylene blue (MB). The device and method can be used quantify and monitor methemoglobin formation in subjects suffering from methemoglobinemia.

Faupel et al. also discloses another example in the U.S. Pat. No. 6,975,899. The '899 patent teaches an apparatus and method to combine more than one optical modality (spectroscopic method), including fluorescence, absorption, reflectance, polarization anisotropy, and phase modulation, to decouple morphological and biochemical changes associated with tissue changes due to disease, and thus to provide an accurate diagnosis of the tissue condition.

Another example can be found in U.S. Pat. No. 6,697,652. The '652 patent utilize a plurality of spectroscopic techniques to measure characteristics of tissue useful in the diagnosis of disease. Fluorescence, reflectance and light scattered spectra can be measured and processed to determine the size, distribution and/or composition of tissue. The methods and systems can be used particularly in the early detection of carcinoma within tissue in vivo and in vitro.

Yet another example is shown in U.S. Pat. No. 5,785,658 issued to Benaron et al. Benaron teaches a tool for nondestructive interrogation of the tissue including a light source emitter and detector which may be mounted directly on the surgical tool in a tissue contacting surface for interrogation or mounted remotely and guided to the surgical field with fiber optic cables. The light source may be broadband and wavelength differentiation can be accomplished at the detector via filters or gratings, or using time, frequency, or space resolved methods. Alternatively, discrete monochromatic light sources may be provided which are subsequently multiplexed into a single detector by time or by frequency multiplexing. The optical sensing elements can be built into a surgical tool end effector tip such as a tissue-grasping tool which has cooperating jaws (bivalve or multi-element). In an example, the light source (or the fiber optic guide) mounted on one jaw and the detector (or fiber optic guide) is mounted in the opposing jaw so that the light emitter and detector are facing one another either directly (i.e., on the same optical axis when the tool is closed) or acutely (i.e., with intersecting optical axes so that the light emitted is detected). In this case, the sensor is working in a transmission modality. Arrangements with the optical components mounted on the same member of a single member or a multi member structure, operating in a reflective modality, are disclosed.

Finally, United States Patent Application Publication number 20070054339 teaches methods that are provided for detecting biomolecular interactions. The use of labels is not required and the methods can be performed in a high-throughput manner. The '339 application also relates to optical devices.

However, for all of the technologies mentioned above, a surgeon cannot evaluate the surgical specimen until the procedure is completed and prostate extracted. Though intraoperative frozen section pathologic analysis of a few select tissue fragments from the prostate or surgical site can be obtained, it is time consuming and costly. Concrete conclusions based on such samples are unreliable, as they do not reflect the entire surgical margin status.

Therefore, a technology and technique are needed to interrogate the tumor percutaneously that reduces the false negative rate associated with needle biopsy and that assesses the surgical margin in real time to confirm complete surgical excision would reduce the number of patients undergoing surgery for small kidney or masses while improving the surgical outcome of those who do. A technology that can reduce unnecessary surgery for benign tumors and the incidence of positive surgical margins would significantly reduce kidney tumor surgery and recurrence/progression rates after surgery.

As such, it would also be highly desirable to develop an integrated optical spectroscopic method that will allow the surgeon in real time to detect prostate adenocarcinoma both on the surface of the prostate and a few millimeters beneath the surface for accurate excision of the gland during laparoscopic prostatectomy. Such a technology that can reduce the incidence of positive surgical margins would significantly reduce prostate cancer recurrence and progression rates after surgery.

The present inventors recognize these needs, and the present invention overcomes the disadvantages of the above-mentioned technologies.

SUMMARY OF THE INVENTION

The present invention includes a tri-modal optical spectroscopy using light-scattering reflectance, time-resolved auto-fluorescence and diffuse near infrared spectroscopy (NIRS). The present invention enables surgeons to intra-operatively demarcate prostate or kidney cancer over the entire resected prostate or kidney so as to significantly reduce positive surgical margins and prostate cancer recurrence after surgery It is a goal of the present invention to characterize optical signatures of cancer both on top and a few millimeters within the prostate gland and kidney tissues by quantifying tissue hemoglobin concentrations and light-scattering particle sizes.

In an embodiment, the present invention is an integrated optical sensing system that measures light reflectance spectroscopy from the prostate gland and kidney tissue with different source detector separations, and the spectroscopic data can be used to differentiate the prostate and kidney cancerous tissue from normal tissue. In an embodiment, the present invention uses both empirical and model-based data analysis to characterize the surface light reflectance and the reflectance from a few millimeters within the tissue.

In one aspect, the present invention is an optical spectroscopy system typically used in differentiate malignant tumors from benign tumors of one or more tissues having at least one electromagnetic radiation source for illuminating one or more tissues, an intraoperative optical probe connected to the electromagnetic radiation source and adapted to transmit electromagnetic radiation from the electromagnetic radiation source to illuminate the one or more tissues and adapted to relay a light-scattering reflectance, a time-resolved auto-fluorescence and a diffuse near infrared emission, a detector connected to the intraoperative optical probe and adapted to capture and receive the light-scattering reflectance, time-resolved auto-fluorescence and diffuse near infrared emission from the one or more tissues, and a computer device connected with the detector. The computer device has one or more tissue classification algorithms that differentiate a malignant tumor from a benign tumor.

In another aspect, the present invention has one or more displays to display projections of the light-scattering reflectance, time-resolved auto-fluorescence and diffuse near infrared emission from the illuminated one or more tissues and display results of tissue classification from the computer device. The one or more tissues imaged can be a normal tissue, a malignant tumor, a benign tumor or any combinations thereof. Typically, the malignant or the benign tumor is a kidney or a prostate tumor. In some aspects, the intraoperative optical probe can be a cystoscope, ureterscope, or a fiber optic endoscope with at least nine individual fibers, and at least one of the individual fibers transmits white light from the electromagnetic radiation source, at least one of the individual fibers connected to the detector used for measuring light-scattering reflectance, at least one of the individual fibers used for measuring time-resolves autofluorescence, and at least one of the individual fibers used for measuring diffuse near-infrared reflectance.

Yet in another aspect, the one or more tissue classification algorithms include algorithms that determine one or more physiological parameters a few millimeters below a surface of the one or more tissues using equation:

$$R(\rho, z_0) = \frac{I_0}{4\pi}\left[z_0\left(\mu_{eff} + \frac{1}{r_1}\right)\frac{\exp(-\mu_{eff}r_1)}{r_1^2} + (z_0 + 4AD) \times \left(\mu_{eff} + \frac{1}{r_2}\right)\frac{\exp(-\mu_{eff}r_2)}{r_2^2}\right]$$

and the present invention also includes algorithms to determine one or more physiological parameters of the one or more tissues within one millimeter from a surface of the one or more tissues using equation:

$$\mu'_s(\lambda) = \left(1 - \frac{d_0^{1/2}}{d_s^{1/2}} \frac{\lambda - \lambda_{min}}{\lambda_{max} - \lambda_{min}}\right) \mu'_s(\lambda_{min})$$

Yet in another aspect, the one or more tissue classification algorithms further includes minimal distance method and a support vector machine algorithm.

In some aspects, the present invention describes a method to differentiate malignant tumors from benign tumors of one or more tissues by interrogating the one or more tissues with a directed electromagnetic radiation having a light-scattering reflectance, a time-resolved auto-fluorescence and a diffuse near infrared emission, detecting the light-scattering reflectance, the time-resolved auto-fluorescence and the diffuse near infrared emission from the one or more tissues using a detector, characterizing the one or more tissues by performing one or more computational operations on the detected light-scattering reflectance, time-resolved auto-fluorescence and diffuse near infrared emissions to determine physiological parameters of the one or more tissues. The one or more tissues can include normal tissue, a malignant tumor, a benign tumor or any combinations thereof, and the malignant or the benign tumor can include a kidney or a prostate tumor.

In some aspects, the step of performing one or more computation operations includes performing calculations to determine physiological parameters a few millimeters below a surface of the one or more tissues using the equation:

$$R(\rho, z_0) = \frac{I_0}{4\pi}\left[z_0\left(\mu_{eff} + \frac{1}{r_1}\right)\frac{\exp(-\mu_{eff}r_1)}{r_1^2} + (z_0 + 4AD) \times \left(\mu_{eff} + \frac{1}{r_2}\right)\frac{\exp(-\mu_{eff}r_2)}{r_2^2}\right]$$

or by performing calculations to determine physiological parameters of the one or more tissues within one millimeter from a surface of the one or more tissues using the equation:

$$\mu'_s(\lambda) = \left(1 - \frac{d_0^{1/2}}{d_s^{1/2}} \frac{\lambda - \lambda_{min}}{\lambda_{max} - \lambda_{min}}\right) \mu'_s(\lambda_{min})$$

The step of performing one or more computation operations can further include calculations using minimal distance method and support vector machine algorithm.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
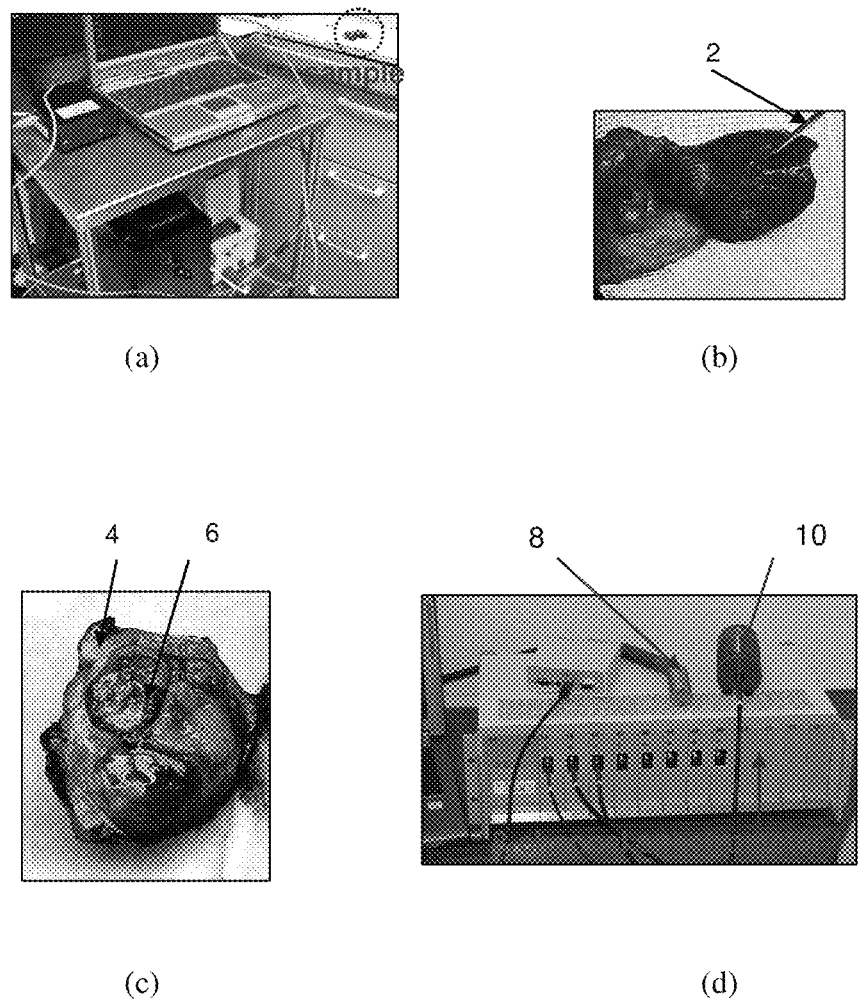
FIGS. 1(a)-1(d) are pictures showing the spectrometer-based setups used for NIR reflectance measurements.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Optical spectroscopy of tissues provides spectral fingerprints of tissue types and can be used to differentiate cancerous tissues from healthy tissues. In recent years, a variety of spectroscopic approaches, such as elastic light-scattering reflectance, auto-fluorescence, and low-coherent interferometry have been developed for local detection and diagnosis of various kinds of cancers and tumors.

Light scattering reflectance (LSR) can be referred to several optical spectroscopic techniques, such as elastic scattering spectroscopy with un-polarized and polarized light, angle-resolved low-coherence interferometry, and coherent backscattering spectroscopy. All of these techniques utilize small-distance light reflectance measurements and examine changes in spectral, angular, and polarization characteristics of light scattered from tissue. Most of these techniques were developed to identify tissue types, diagnose diseased tissues, and differentiate cancerous tissues from healthy tissues. Overall, LSR has a proven capability to differentiate tissue types and diagnose tissue abnormalities at the local measured site, with a penetration depth of ~1-2 millimeter using unpolarized near infrared light.

Specifically, in the case of renal cancer, the clinical and histological findings and those of other groups show that these tumors feel hard to touch, due to their high cell density and collagen content. They also appear white/yellow in color as they have lower microvessel density compared to normal renal tissues and contain necrotic regions. These histological attributes translate to higher light scattering and lower light absorption compared to normal kidney, consistent with the NIR reflectance findings.

Open radical prostatectomy (ORP), a standard treatment for clinically localized prostate cancer has been shown to be an efficacious treatment in multiple studies. However, unlike most other solid tumors, prostate cancer is often not palpable or visible during surgery. In fact, positive surgical margins (PSM) are not an infrequent occurrence. Depending on the pathologic tumor stage, PSM rates in contemporary clinically localized prostate cancer series range from 5 to 50%. As expected, patients whose pathologic specimen has a positive margin have a higher likelihood of disease recurrence and a poorer prognosis. Therefore, minimizing PSM rates while preserving vital adjacent structures such as the urinary sphincter and the erectile neurovascular bundles, remains a challenge.

Though the advent of laparoscopic radical prostatectomy (LRP) has provided several advantages to the patient and surgeon including improved visualization (10-20× magnification), the rate of incomplete tumor excision reflected by PSMs remains unchanged and highly variable. Many clinicians believe that tumor excision is a function of tumor biology (microscopic extension), prostatic anatomy (poor definition of the prostatic capsule), and lack of discriminatory tactile sensation. Though intra-operative frozen section pathologic analysis of select tissue fragments from the prostate or surrounding structures is currently employed to address these limitations in ORP and LRP, they clearly do not reflect the entire surface area of the resected specimen. Sampling errors are significant and cannot be avoided when using conventional frozen section analysis. Furthermore, processing of pathologic specimens for frozen section analysis is both time consuming (10-20 min) and costly (processing costs plus operative time costs).

Tissue auto-fluorescence: Fluorescence emission, in contrast to light scattering methods, is shifted towards longer wavelengths comparing to the impinging illumination. This allows using cut-off filters and monochromators to observe the phenomenon in practically dark background. Fluorescence studies are usually carried in two categories: a steady state and time-resolved modes. In the steady-state mode, the intensity of emission is collected as function of wavelength which results in fluorescence spectra, characteristic for examining chromophores. Autofluorescence spectrum of tissue with UV excitation contains components related to tryptophan, NADH, flavins, and others. A proper excitation should be used to register emission of a particular component. In the time-resolved mode, the intensity is detected as a function of time, and fluorescence is delayed comparing to the excitation (again, in contrast to the scattering). Each fluorophore has its characteristic lifetime, which in addition to the spectra gives another opportunity for fluorescence species differentiation. The advantage of the latter mode is the intrinsic nature of lifetime measurements, independent of the intensity of excitation light, providing clear fingerprints for cancer identifications.

In the last 1-2 decades, steady state, auto-fluorescence with UV excitation has been broadly developed and investigated as an in vivo, real time, diagnostic tool to detect a variety of cancers. A few examples include the detection of cervical cancer, skin cancer, colon cancer, and gastric cancer. Similar fluorescence-based methods have been investigated as intra-operative tools to assist neurosurgeons for better visualization of the brain tumor margins with and without the contrast-enhancing approach. It is seen that with injection of 5-aminolevulinic acid, the fluorescence signal from the tumor was highly enhanced, enabling to improve resection completeness and decreasing the amount of residual tumor post-resection. While auto fluorescence, without any injection of enhancement agent, seemed not able to identify the positive tumor margins effectively, a combination with light reflectance did improve the accuracy of tumor identification. On the other hand, time-resolved fluorescence measurements for cancer detection have been conducted in two major areas: fluorescence lifetime microscopy and imaging using ex vivo samples and in vivo animal models, and non-invasive breast cancer detection using the frequency-domain approach. There is little report on using fluorescence lifetime as an imaging or diagnostic marker for in vivo cancer identification and tumor demarcation in the United States.

Example

Kidney Tumors

Spectroscopic data from the human kidney and kidney tumors immediately after radical or partial nephrectomy, the present example uses a single-channel spectrometer (FIG. 1(a)) for optical and NIR light-scattering reflectance measurements with a needle-like probe having a source-detector separation of 0.2 mm (FIG. 1(b)). Measurements were performed both on the outside of the tumor and resection margin areas. Subsequently the resected specimens were cut open and measurements were performed directly onto the tumor nodules and on resection margins (FIG. 1(c)). In one embodiment, the present example uses an 8-channel spectrometer in for simultaneous measurements of up to 8 different source-detector separations (FIG. 1(d)). The single- and multi-channel spectrometers can detect light in the wavelength regions of 350-1100 nm and 350-900 nm, respectively. Before fixing the excised specimen, light scattering reflectance spectra were taken at multiple locations at the cross section (FIG. 1(c)). Confirmation of cancer came from the final histology report, which is a "gold standard" to derive correlations between differences in optical properties and tissue pathology.

Figure 2:
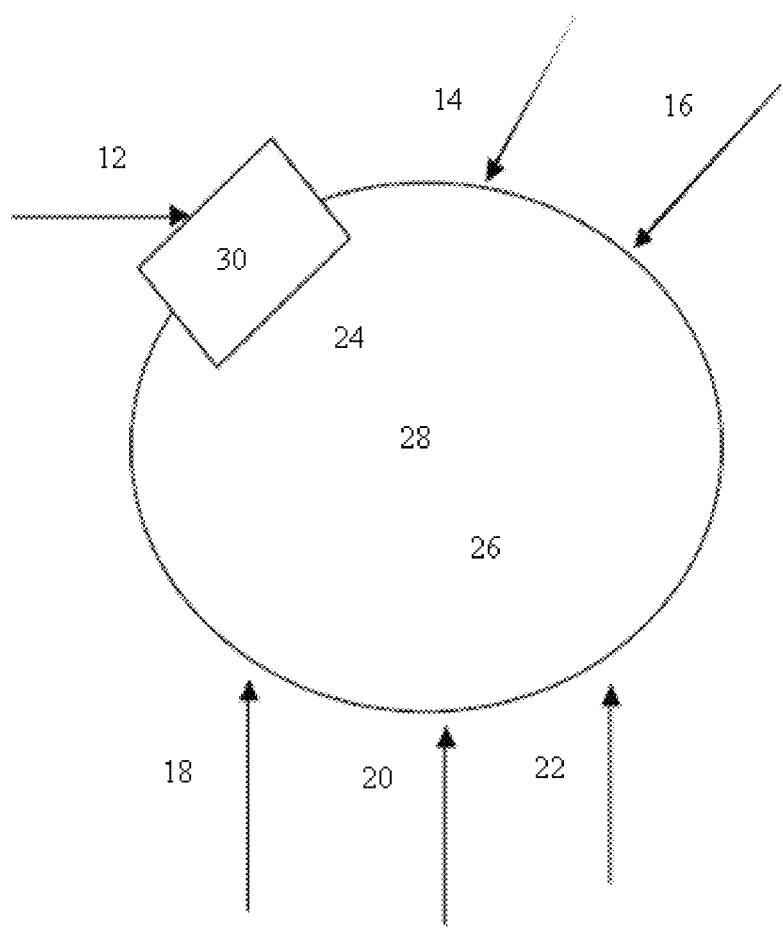
FIG. 2 is a schematic for the measurement protocol for the excised normal kidney and tumor samples.

FIG. 1 shows two spectrometer-based setups used for NIR reflectance measurements: (a) a single-channel spectrometer, and (d) an 8-channel one; (b) Placement of the single-channel probe on a resected kidney tumor sample; (c) NIR measurements locations for a resected sample that has been cut open. The outer margins appear dark due to ink that pathologists use to keep track of surgical margin locations in histology slides. Light Reflectance from Ex Vivo Human Kidney Cancer Samples The protocol for the excised normal kidney and tumor samples from partial nephrectomies is shown in FIG. 2. The numbering of the reflectance measurement locations indicates whether they were performed on the tumor capsule (locations #2, #3), on the surgical margin (locations #4, #5, #6), the center of the resected tumor (locations #7, #8) or some residual fat left on top of the capsule (location #1). Data were collected from radical nephrectomies where measurements were performed on the normal kidney capsule, the tumor capsule and the tumor center. However, the radical nephrectomy data was analyzed separately from partial nephrectomy data.

Figure 3:
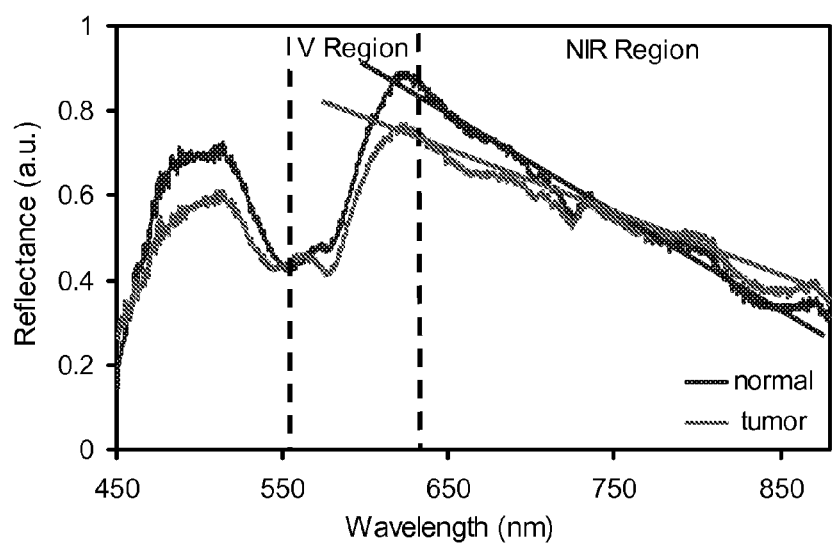
FIG. 3 is a plot of the reflectance curves from tumor samples (red) and normal parenchyma (blue)

FIG. 3 shows light scattering reflectance spectra measured by placing the needle-like probe (FIG. 1b) on an excised kidney cancer that has been cut open (as in FIG. 1c). The curves were calibrated with a standard white sample. The observed spectra originated from healthy parenchyma and the other from cancerous tissues were confirmed with pathology report. Slopes of spectrally-resolved reflectance in the 560-630 nm and 630-880 nm ranges as putative indices for differentiation between healthy and cancerous tissues were selected for use.

Figure 4:
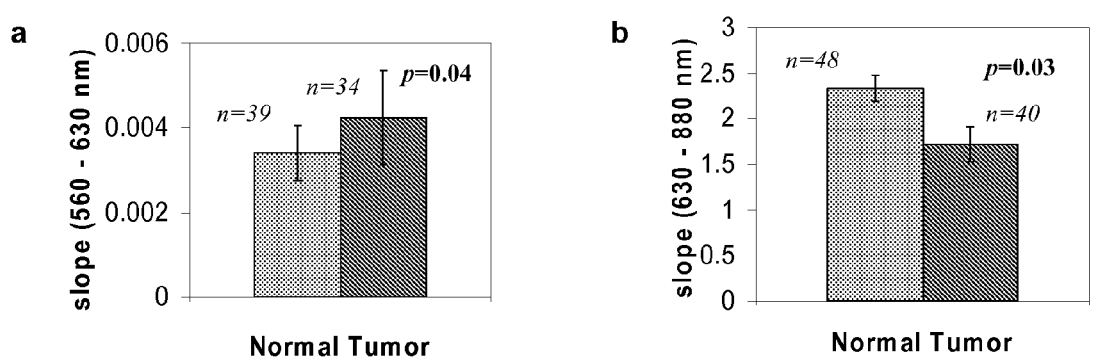
FIGS. 4(a)-4(b) are plots showing the slope of spectral reflectance was significantly different between normal (blue bars) and tumor (dark purple bars) tissues for both 560-630 nm and 630-880 nm.

Approximately 20 kidney tumors and performed multiple measurements per tumor were measured. FIGS. 4a and 4b show that the slopes in both spectral ranges have statistically significant differences ($p<0.05$) and therefore have good potential to differentiate between tumor and normal tissue.

Figure 5:
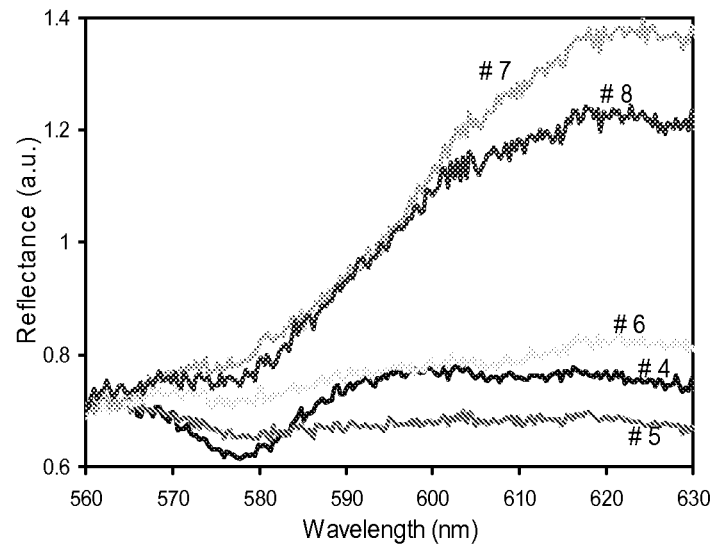
FIGS. 5(a)-5(b) are plots showing partial optical spectra in the visible region.
Figure 5:
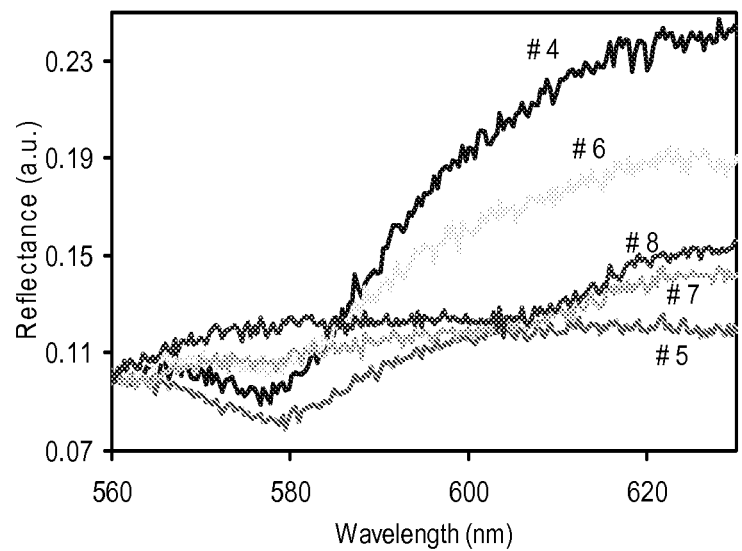

Furthermore, besides the proposed reflectance slope method, the present inventors compare and correlate the reflectance spectral shapes to identify cancer renal tissues from normal tissues. For example, FIGS. 5a and 5b are taken from two different patients that underwent partial nephrectomies. FIGS. 5a and 5b show spectral reflectance curves in the 560-630 nm range obtained inside the tumor locations (#7 and #8) and on the surgical margins (#4, #5, and #6). Histological analysis proved that both tumors were malignant, but the thinnest resected surgical margin (#5) was negative in case (a) (FIG. 5a), but positive in the other (FIG. 5b). The optical measurements are consistent with these histological findings: the spectrum of margin #5 in case (a) follows the same spectral feature as those of normal kidney parenchyma (#4 and #6), while the spectral feature of #5 goes along with those of tumors at #7 and #8 in case (b).

To be more quantitative for the comparison, Pearson correlation coefficients, r, was used to identify the differences between normal and cancerous tissues in the visible region within each individual radical nephrectomy specimen. Pearson correlation coefficients are close to 1 (excellent correlation) for the spectra made at different locations within the tumors (mean $r=0.968$) and for the spectra made within normal parenchyma sections (mean $r=0.88$). On the other hand, the correlation parameters were very poor between the tumoral and non-tumoral tissue spectra (mean $r=0.07$). In the subset of partial nephrectomies, an excellent correlation between intra-tumoral measurements (mean $r=0.94$) were found. In addition, there was a close correlation among measurements made on the normal parenchyma margin of the tumor (mean $r=0.94$) except in the one case of a positive margin (oncocytoma), as shown in FIG. 5a, where the measurement from the site of the presumed positive margin did not correlate with the adjacent parenchyma margin (mean $r=0.48$, FIG. 5a). Furthermore, in that specific case, the measurement made at the site of the positive margin correlated well with the intra-tumoral measurements (mean r=0.8). Of note, the spectra in FIGS. 5a and 5b show a spectral feature discrepancy between normal and cancerous tissues because the tumors have different histology (5a is clear cell carcinoma and 5b is oncocytoma).

Table 1 gives the comparison for the Pearson correlation coefficients that are evaluated between pairs of locations: surgical margin location is #5, tumor center locations are #7 and #8. The highlighted row in Table 1 shows the correlation coefficients between #5 and #7, #8, which are in fact more than twice than that of any negative margin measurement. Moreover, the slopes listed are consistent with the description given above.

TABLE 1

| Tumor | Slope of curve #5 | Correlation between #5 & #7 | Slope of curve #7 | Slope of curve #5 | Correlation between #5 & #8 | Slope of curve #8 |
|---|---|---|---|---|---|---|
| 1 | 2.66 | 0.004 | 2.28 | 2.66 | 0.01 | 2.48 |
| 2 | 2.65 | −0.23 | 2.09 | 2.65 | −0.09 | 2.22 |
| 3 | 1.5 | 0.75 | 1.05 | 1.5 | 0.88 | 2.04 |
| 4 | 2.45 | 0.37 | 1.25 | 2.45 | 0.34 | 1.08 |
| 5 | 3.39 | 0.14 | 2.03 | 3.39 | 0.29 | 1.07 |
| 6 | 2.75 | 0.28 | 1.92 | 2.75 | 0.19 | 2.15 |
| Mean | 2.8 | 0.22 | 1.3 | 2.8 | 0.18 | 2.12 |
| Stdev | 0.58 | 0.04 | 0.38 | 0.58 | 0.03 | 0.42 |
| SEM | 0.25 | 0.02 | 0.17 | 0.25 | 0.01 | 0.18 |

From the results shown above, the second method, i.e., the correlation method are based on the visible light reflectance spectra, required a standard (calibration) spectrum from the normal tissue so that an unknown tissue could be identified as either tumor or non-tumor by quantifying its correlation to the standard spectrum. This method can be complementary to the spectral slope algorithm to increase accuracy of tumoral tissue identification. A standard spectrum from normal renal tissue can be easily obtained from a known control region during surgery.

Identification Between Benign and Malignant Renal Tissues

Figure 6:
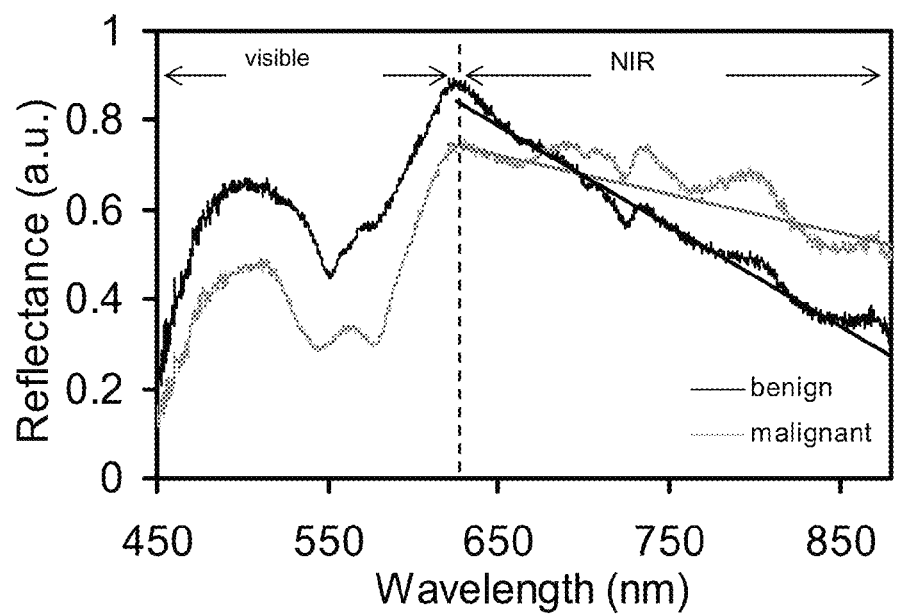
FIG. 6 is a graph showing the average spectra taken from the benign tumors (black curve, mean of 12 benign tumor sites) and from malignant tumors (grey curve, mean of 28 malignant tumor sites)
Figure 7:
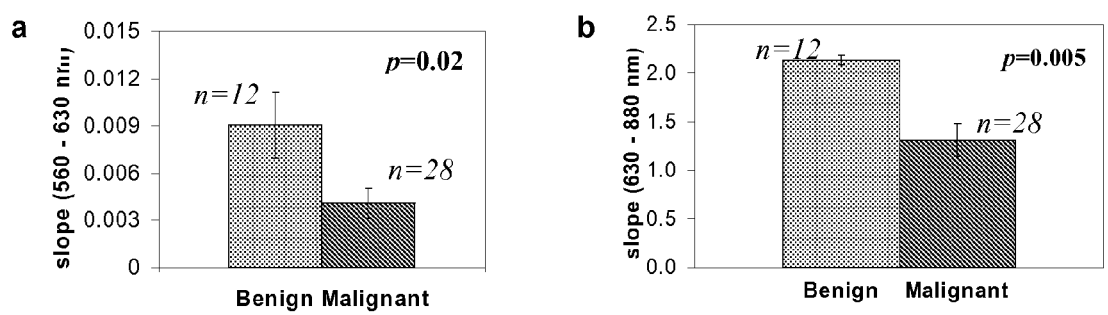
FIGS. 7(a)-7(b) are plots of the slope of spectral reflectance that are significantly different between benign (blue bars) and malignant (dark purple bars) tissues for both the 560-630 nm and 630-880 nm regions.

The slope method, in addition to differentiating between normal and tumor tissues, could differentiate between benign and malignant tumor types. FIG. 6 demonstrates this point. Statistically significant differences in slopes were found for both the visible (FIG. 7a) and near infrared (FIG. 7b) ranges when comparing light reflectance measurements from benign versus malignant tumors as classified by histology.

Figure 8:
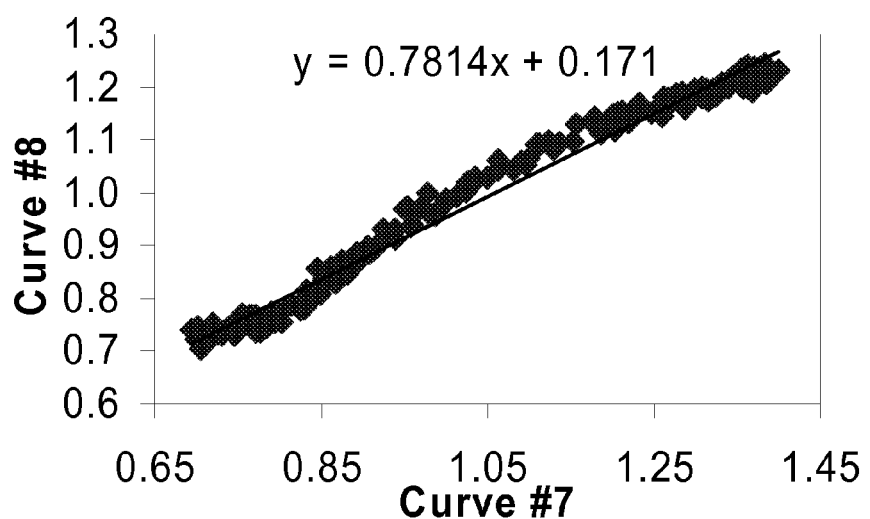
FIG. 8 is a plot of a correlation curve between two normalized reflectance across all wavelengths in the 560-630 nm range obtained from two different locations within tumor samples that have been cut open.

Extensive statistical analysis was done to demonstrate correlations in the raw reflectance data between measurements at different tumor or surgical margin locations. Typical results of these analyses are shown in FIG. 8: measurements within the same tissue type, e.g. the benign tumors, are very well correlated (FIG. 8) even when pooling results from different samples.

Figure 9:
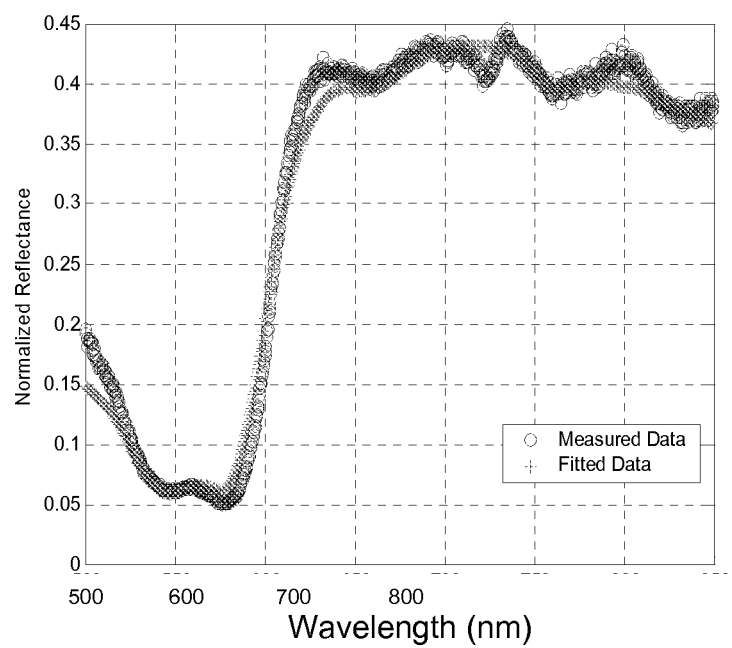
FIG. 9 is a plot of a comparison graph between the data taken from the optical reflectance of an ex vivo renal specimen and the model. The latter one can provide estimates of $HbO_2$, Hb, and light scattering coefficients of the probed tissue volumes.

Model Fitting for Light Scattering Coefficients to Differentiate Cancerous and Normal Renal Tissues In addition, a recent theoretical development in light scattering is consistent and affords to predict the light reflectance spectra with known optical properties. The present inventors used an analytical expression for light reflectance to recover the optical and physiological parameters of kidney cancers both ex vivo and in vivo. A sample of these efforts is shown in FIG. 9, which was taken from an ex vivo sample. It is seen that the model (red curve) can fit well the data (blue curve). The model fit produces estimates for the concentrations of oxy- (HbO2) and deoxy-hemoglobin (Hb), and the spectrally-resolved transport scattering coefficients of probed tissue volumes. Due to the needle-like probe's source-detector separation of 0.2 mm, only a small superficial tissue volume near the detector fiber is probed.

Figure 10:
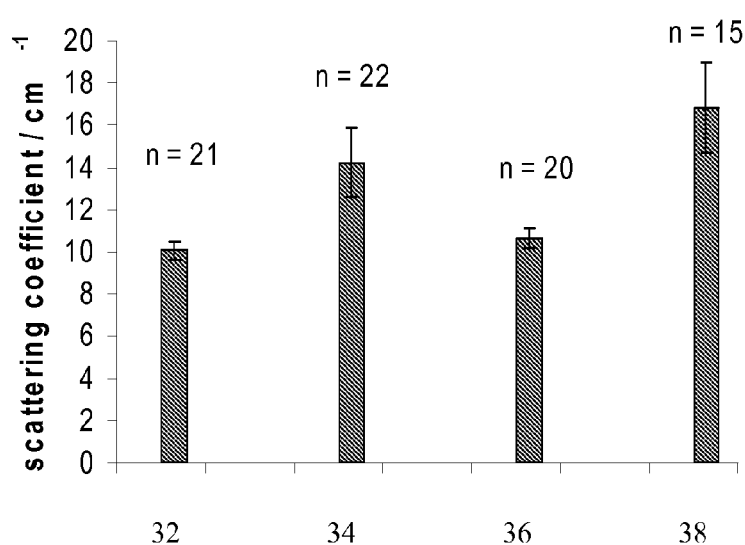
FIG. 10 is a plot showing differences in scattering coefficient between tumor and normal kidney tissues.

FIG. 10 shows the scattering coefficient fitting results at 500 nm for measurements performed both on the normal kidney capsule (Outside Capsule) and the tumor surface (Outside Tumor) as well as at the center (Inside Tumor, Inside Normal) of both tumor and normal kidney, after these tissues were cut open. The tumor scattering coefficient is shown to be significantly higher than that of normal kidney both for measurements on the periphery and at the center. These results are consistent with histological findings of higher cell density and collagen content for kidney tumors and indicate that the scattering coefficient can be an additional data type to be entered into the tissue classification algorithms. The Hb and $HbO_2$ fitting results were less conclusive as there was no easy way to prevent exposure of the potentially hypoxic tumor center to atmospheric air once the ex vivo samples were cut open.

Auto-Fluorescence from Ex Vivo Human Kidney Specimens

Figure 11:
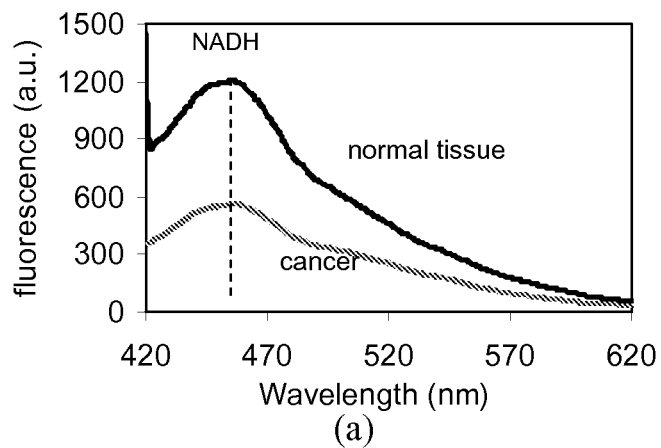
FIG. 11(a) is a autofluorescence spectra from a cancerous (pink curve) and normal tissue (black curve) region of an excised kidney cancer cross section. The main peak is at 460 nm due to fluorescence from NADH.
FIG. 11(b) is a normalized product spectra of autofluorescence and light scattering reflectance: pink curve is for cancer and black curve for normal tissue.
FIG. 11(c) is a ratio spectra between autofluorescence and scattering reflectance (pink for cancer)
Figure 11:
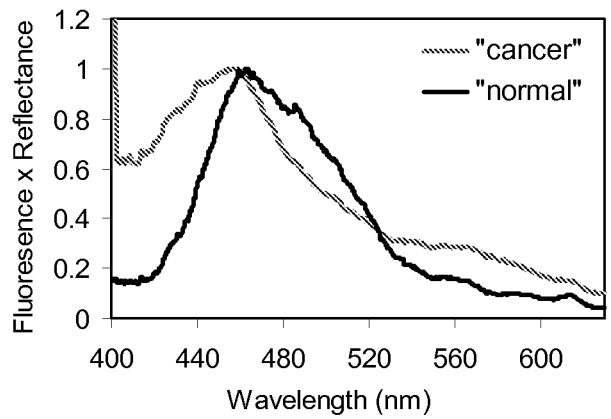
Figure 11:
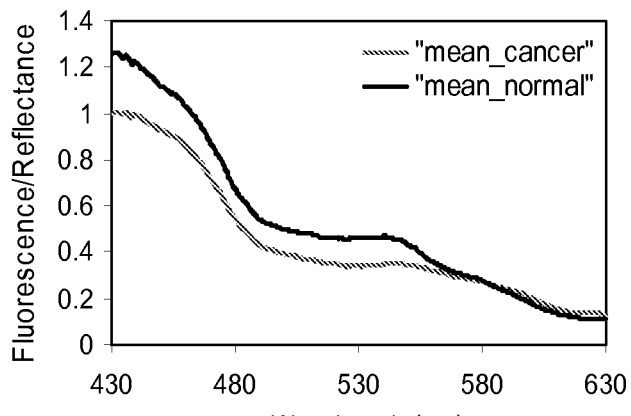

Using a similar needle-like probe to the one used for the reflectance readings auto-fluorescence from excised kidney cancer cross sections was measured (FIG. 1c). The fluorescence excitation source was a broadband UV lamp with a cut-off filter at 400 nm placed in front of it, so that only 400 nm and below could be delivered to the specimen. The UV light was collimated and delivered through a bifurcated 1-mm fiber probe tip, and the detected autofluorescence was collected and sent to the single-channel spectrometer (FIG. 1a). While the detected spectral range was 350-1100 nm, UV-visible region was the focus, where NADH has a strong auto-fluorescence peak (at 460 nm). This portable fluorescence measurement system was calibrated against a standard laboratory fluorometer before processing the ex vivo kidney data. FIG. 11a shows two calibrated, steady-state autofluorescence spectra taken from a region of cancer and normal kidney parenchyma, exhibiting a strong peak at 460 nm due to NADH. However, the two curves differ only in amplitude, with no other distinct aspects found between them. Then, the autofluorescence signals were combined with the scattering reflectance (FIG. 2), either multiplying them (FIG. 11b) or dividing the fluorescence by the reflectance (FIG. 11c). As seen in both FIGS. 5b and 5c, the difference in spectroscopic features between cancer and normal tissues is still not that large, meaning that spectroscopically, the steady-state autofluorescence measurement is not an optimal choice since it heavily relies on intensity changes. Another method that is more sensitive to intrinsic properties of tissues would be desirable.

Figure 12:
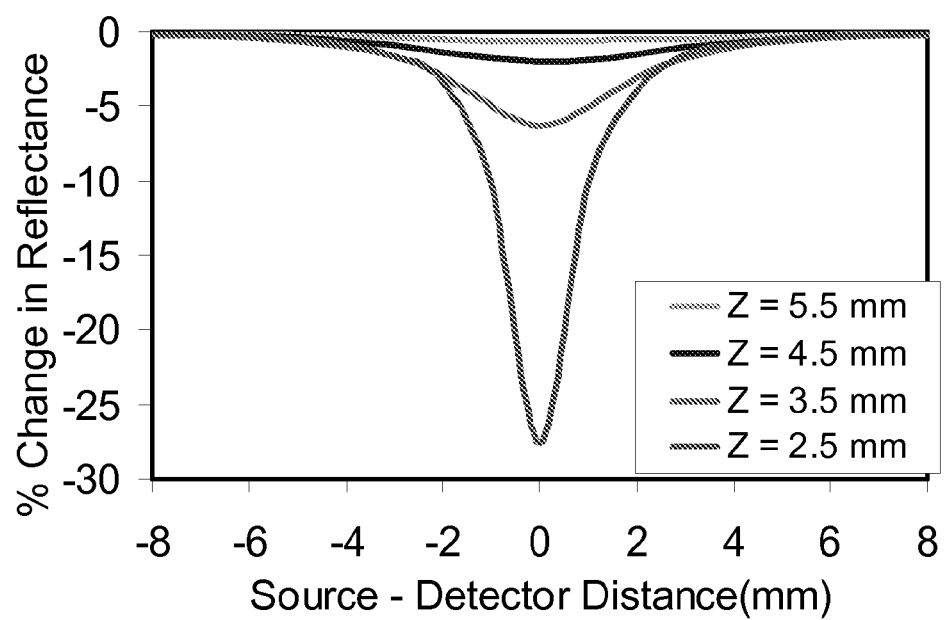
FIG. 12 is a plot of simulated changes in reflectance due to a hidden object (5×5 mm3 in size) at a depth Z below the surface.

Monte Carlo Simulations to Estimate the Detection Sensitivity of Different Tissue Heterogeneities for Different Probe Design Scenarios As part of the efforts to design an optimal optical spectroscopic probe, Monte Carlo (MC) simulation of optical and NIR photon propagation through a spatially uniform scattering medium with a 5.5 mm$^3$ highly absorbing object was used, having similar optical properties to those of venous blood. The object was placed at variable depths (Z) and the source-detector separations were varied from 0 to 8 mm. The percentage change in reflectance due to the absorber was recorded. FIG. 12 demonstrates the MC-simulated calculation of percentage changes in reflectance at 720 nm with increasing object depth. Simulations of this nature are used to explore in detail the sensitivity in detecting tissue heterogeneities of different sizes and optical properties from reflectance measurements made by the probe, for different design scenarios.

Classification Algorithms to Demarcate Kidney Cancer

The Minimal Distance Method (MDM) is a statistical matching process used in pattern recognition for remote sensing and image processing. Class assignment follows minimization of the Euclidan (linear) or Mahalanobis (correlated) distance. It was found that Mahalanobis distance to be useful given that it is scale-invariant and accounts for correlations within data sets. Furthermore, the Support Vectors Machine (SVM) has found great utility in machine learning. It is a supervised learning algorithm that recognizes subtle patterns contained in complex data sets. SVM is an effective classifier, and has been used with increasing frequency in recent years.

Both MDM and SVM were used as classification algorithm. In parameter selections, up to 6 parameters were picked and were derived from light-scattering reflectance and model fitting. These parameters are index 1 (slopes in the visible region), index 2 (slopes in the NIR region), index 3 (correlation coefficients), HbO$_2$, HbT, and $\mu_s'$, labeled as A1, A2, A3, B1, B2, and B3, respectively. In the simulated classification runs, generated 240 uniformed distributed sample points for each of A's and B's were generated with a uniformly distributed random numbers in the range of mean±S.D. For each set, 211 points were used to train the classifiers, and the rest 29 samples for each set were available for testing the performance of the classification algorithms. Next, 2 parameters were selected (such as A1 and B1, A2 and B3, or A3 and B2) out of the 6 parameters to determine classification success rates in comparison to the rate with all 6 parameters used.

FIG. 13a shows an example how to label the classified tissue type: "1" for normal tissue and "0" for cancer. In this case, all normal tissues are correctly identified, while 5 out 29 cases were missed for cancer, with a success rate of 100% and 83% for normal and cancer, respectively, namely, specificity is 100% and sensitivity is 83%. This set of data was obtained using SVM.

Among A's and B's, to determine how many of them are needed to provide an accurate classification, 45 sets of 2 parameters, 6 random sets of 4 parameters, and the complete set of 6 parameters were selected and calculated the respective success rates, as shown in FIG. 13b. It is clearly seen that more parameters do provide better accuracy in classification of both normal tissue versus cancer.

Methods

Figure 14:
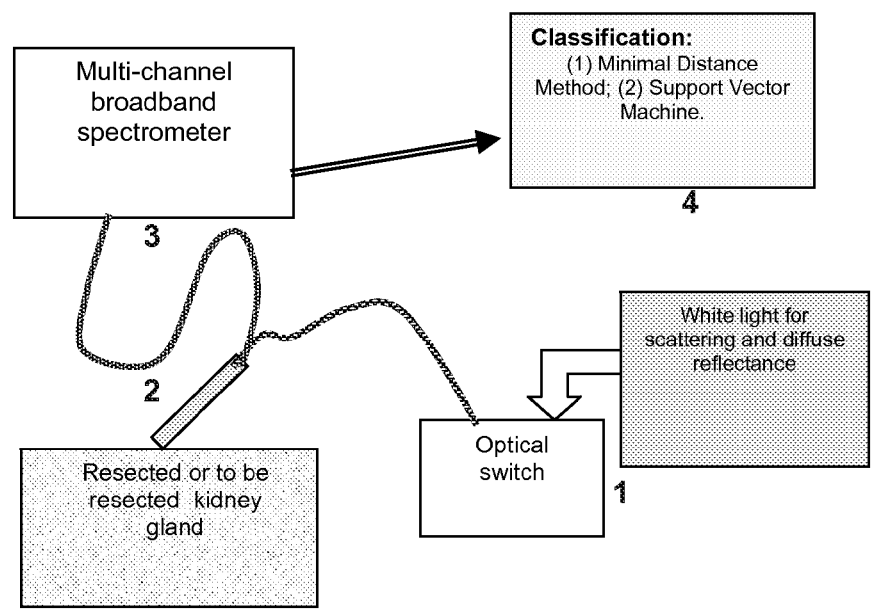
FIG. 14 is a schematic of the overall system design.

FIG. 14 shows the overall optical spectroscopic system design: 1) optical light source and switch, 2) intra-operative probe, 3) multi-channel spectrometer, and 4) classification algorithms for the identification of kidney cancer.

Measurements Taken on Ex Vivo Human Kidney Specimens

Using existing spectroscopic system, the present inventors measured optical and NIR diffuse reflectance from ex vivo human kidney tumor specimens with the needle-like probe (FIG. 1a). In particular, the measurements take place within 10 minutes, or less, after nephrectomy so that tissues have not denatured much. In addition, the present inventors performed the measurements before and after cutting open the resected human kidney tumors to obtain the optical signatures of healthy parenchyma margins and those of kidney tumors. Spectral features of light scattering reflectance were quantified in order to illustrated the quantities of oxygenated (HbO$_2$), deoxygenated (Hb), total hemoglobin (HbT) and water (H$_2$O) concentrations, and the reduced light scattering coefficient ($\mu_s'$) for both internal and external areas. Tracks of the spatial location were kept where optical measurements are performed on each sample in a way that allows the present inventors to correlate these with histology reports from these same areas.

Figure 15:
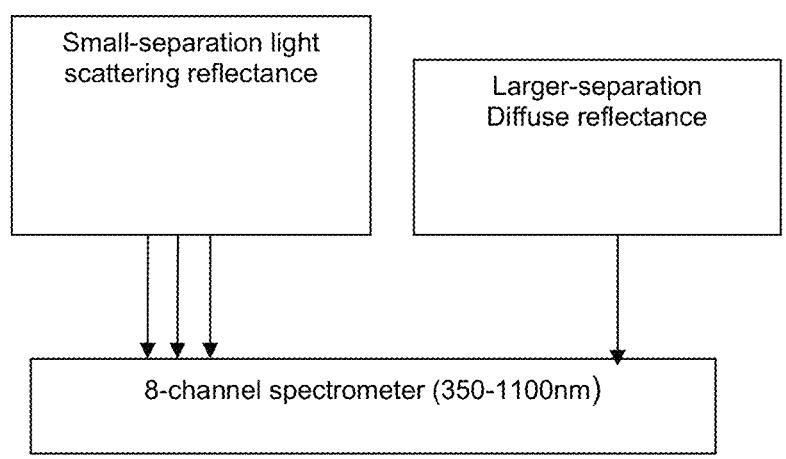
FIG. 15 is a schematic of the implementation steps of the demonstration.

Optimal Design and Implementation of a Multi-Channel Spectrometer with an Intraoperative Optical Probe The present inventors implemented a multi-channel spectrometer in a format similar to that shown in FIG. 1a. The present invention used up to eight channels of the Ocean optics HRD-4000 spectrometer, which has a 16-bit dynamic range and detection sensitivity in the 350-1100 nm wavelength range (FIG. 15). The present invention used three channels to record light-scattering reflectance at needle-like probe distances and one or more channels can be added for future use if a larger detection area is needed.

Figure 16:
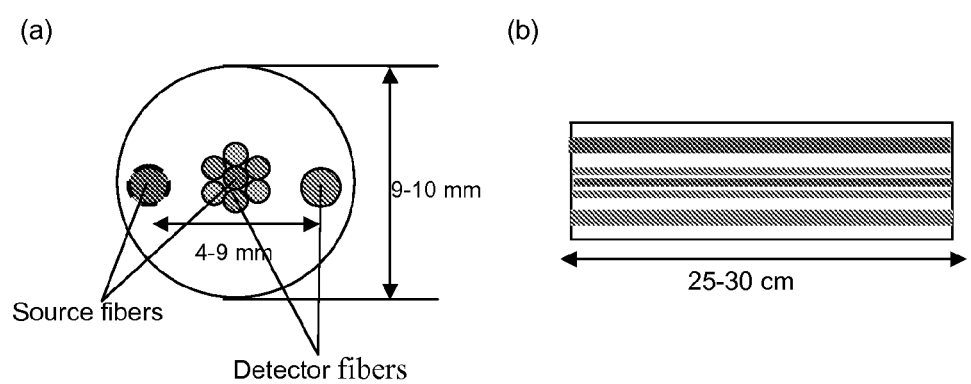
FIGS. 16(a)-16(b) is a schematic of the fiber optic used in the present invention.

Since this demonstration aims to integrate different spectroscopic modalities for intraoperative tissue classification a unified probe that can collect all this information was designed as shown in FIG. 16. The overall outer diameter is about 9-10 mm (cannot exceed 10 mm), so as to be compatible with laparoscopic nephrectomy ports (FIG. 16a) The probe is rigid and about 25-30 cm in length (FIG. 16b). Since there are free spaces available at the probe port besides the currently needed fibers, the present inventors design a few extra fiber channels that can be utilized in the future for versatile applications. There are 9 fibers included in the probe. The 7 fibers at the center are 400 µm in diameter, and the center fiber (red) surrounded by the other six are used to deliver white light from a Tungsten-Halogen source. Three out of six surrounding fibers (green) are connected to the multi-channel spectrometer for light-scattering reflectance measurements. The other three (gray) fibers are free for now, but later can be used with time-resolved autofluorescence measurements (for both continuous and pulsed excitation) for future multi-modality integration. The far-apart fibers are planned also for future utilization when the diffuse reflectance measurements are needed.

The small-separation channels probes tissue volumes that are within ~1 mm depth from the resected sample or surgical margin surface. The larger source-detector separations (only one is shown in FIG. 16 for clarity) probes tissues that are a few millimeters deep under the surface. This way, it enables the interrogation of larger kidney tissue volumes and the ability to obtain their spectroscopic features for cancer classification.

Algorithm to Determine Physiological Parameters of Tissues within One Millimeter from the Tissue Surface For small source-detector separations where the detected light is non-diffuse, a newly developed empirical expression to fit the measured reflectance (R) data was used:

$$R = \cfrac{1}{k_1 \cfrac{1}{\mu'_s} + k_2 \cfrac{\mu_a}{\mu'_s}}$$  Equation (1)

where $k_1$ and $k_2$ are parameters depending on the geometrical characteristics of the optical probe as well as on the refractive indices of tissue and the surrounding medium and can be determined using a tissue physical model. Equation (3) has been shown to be in good consistency with corresponding Monte Carlo simulations and tissue-simulating phantom measurements. The spectral dependence of absorption ($\mu_a$) for blood-perfused tissues can be written as:

$$\mu_a(\lambda) = HbO_2 \ast \epsilon_{HbO_2}(\lambda) + Hb \ast \epsilon_{Hb}(\lambda) + H_2O \ast \epsilon_{H_2O}(\lambda)$$  Equation (2)

where $\lambda$ is the wavelength in nm, $HbO_2$, $Hb$, $H_2O$ represent concentrations of oxy-, deoxy-hemoglobin, and water respectively, and $\epsilon_{HbO2}(\lambda)$, $\epsilon_{Hb}(\lambda)$, $\epsilon_{H2O}(\lambda)$ are extinction coefficients for $HbO_2$, $Hb$, and $H_2O$ at $\lambda$, respectively. Moreover, it is known that the spectral dependence of light scattering ($\mu_s'$) of tissue is weak and can be approximated as the following equation:

$$\mu'_s(\lambda) = \left(1 - \frac{d_0^{1/2}}{d_s^{1/2}} \frac{\lambda - \lambda_{min}}{\lambda_{max} - \lambda_{min}}\right) \mu'_s(\lambda_{min})$$  Equation (3)

where $d_0$ and $d_s$ are effective scatter factors derived from Mie theory, and $\lambda_{min}$ and $\lambda_{max}$ define the range of wavelengths where reflectance measurements are performed. Substitution of eqs. (2) and (3) into eq. (1) results in a quantitative relationship between Hb, $HbO_2$, $H_2O$, $d_s$, $\mu_s'(\lambda_{min})$ and the measured spectrally-resolved reflectance in the 600-1100 nm range. This in turn results in the quantification of HbO, Hb, HbT, hemoglobin oxygen saturation ($SO_2$) and tissue light scattering parameters. The feasibility of this approach in recent work were demonstrated, particularly for tissue light scattering parameters.

Algorithms to Determine Physiological Parameters a Few Millimeters Below the Tissue Surface For diffuse NIR reflectance, diffusion theory and spectroscopic approach were combined to analyze the steady-state diffuse reflectance, R, where R is the diffuse photon flux escaping from the tissue/boundary interface (i.e., at z=0). The reflectance can be measured through the NIRS reflectance and is written as 'R'

$$R(\rho, z_0) = \frac{I_0}{4\pi}\left[z_0\left(\mu_{eff} + \frac{1}{r_1}\right)\frac{\exp(-\mu_{eff} r_1)}{r_1^2} + (z_0 + 4AD) \times \left(\mu_{eff} + \frac{1}{r_2}\right)\frac{\exp(-\mu_{eff} r_2)}{r_2^2}\right]$$  Equation (4)

In the diffusion regime ($\mu_a \ll \mu_s'$), equation (3) has been shown in good consistency with spatially resolved Monte Carlo simulations. Since the spectral dependence of absorption ($\mu_a$) for blood-perfused tissues can be written as:

$$\mu_a(\lambda) = HbO \ast \epsilon_{HbO}(\lambda) + Hb \ast \epsilon_{Hb}(\lambda) + \epsilon_{H2O}(\lambda)H_2O,$$  Equation (5)

where $\lambda$ is wavelength in nm, HbO, Hb, $H_2O$ represent concentrations of oxy-, deoxy-hemoglobin, and water respectively, and $\epsilon_{HbO}(\lambda)$, $\epsilon_{Hb}(\lambda)$, $\epsilon_{H2O}(\lambda)$ are extinction coefficients for HbO, Hb, and $H_2O$ at $\lambda$, respectively. Moreover, it is known that the spectral dependence of light scattering ($\mu_s'$) of tissue is weak and can be approximated as the following equation:

$$\mu_s'(\lambda) = a_s \lambda^{-p_s}$$  Equation (6)

where $a_s$ and $p_s$ are light scattering amplitude and power. By substituting eqs. (5) and (6) into eq. (4), one obtains a quantitative relationship between the parameters of Hb, HbO, $a_s$, $p_s$ and the measured light reflectance from the NIR multispectral images in the wavelength range of 600 nm to 1100 nm. This set of parameters (i.e., Hb, HbO, $H_2O$, $a_s$, $p_s$) can be obtained by fitting the equation with the data, resulting in the final quantification of HbO, Hb, HbT, hemoglobin oxygen saturation, ($SO_2$), light scattering amplitude, $a_s$, and scattering power, $p_s$. This approach to quantify all Hb, HbO, and light scattering coefficients has been also proved by several groups. (see FIG. 6).

Laboratory Phantoms

To demonstrate the optical spectroscopic system with the probe, a tissue phantom consisting of a blood-lipid complex was used. A laboratory phantom was built, consisting of a liquid mix of blood and lipid, which is surrounded by a thin layer. The phantom has a size of 3-4 cm diameter and 2-3 cm in height. It can be oxygenated or deoxygenated by bubbling oxygen or nitrogen gas into the covered phantom so that the parameters of oxy-, deoxy-, and total hemoglobin concentrations can be varied for system testing and validation. By changing intralipid concentrations in the phantom, the present inventors were able to vary light scattering properties for $\mu_s'$ quantification.

Parameter Calibration to Obtain Physiological Parameters of Tissues from the Model In order to fit the physiological parameters, such as Hb, $HbO_2$, $H_2O$, $d_s$, $\mu_s'(\lambda_{min})$, given in eq. (1), the optical system with a chosen probe in order to obtain $k_1$ and $k_2$ were calibrated. To do so, the procedures was following: spectral readings from the tissue samples and white standard have the same integration time; fiber setup and geometry used to take the calibration spectrum from the white standard remain the same as the one used in the $k_1$ and $k_2$ calibration process; the calibration spectrum from the white standard can be retaken using the integration time that matches the actual tissue measurement. In this step, one needs to assure that the distance (or height) between the fiber tip and white standard surface remains the same as that used in the $k_j$ and $k_2$ calibration process.

Development of Classification Algorithms

The classification algorithms used in this work have been adapted from the image processing discipline and have been shown to be both computationally efficient and accurate. Efficiency is necessary for the clinical application proposed in this work as it enables rapid intraoperative data processing. There is no intrinsic limitation to the classification accuracy that these computational methods can provide; the quality of measurements and the amount of independent information contained in the data types derived from these measurements is the ultimate determinant of tissue classification accuracy.

Minimal Distance Method (MDM)

There are two phases in using MDM: the training and classification phase. In the training phase, select respective parameters from the three spectroscopic techniques, such as A's, B's, C's, as diagnostic/classification markers to differentiate cancer from normal tissue; based on the mean values of A's, B's, C's derived from animal and human measurements, compute the center location, P, of the parameters in the multi-dimensional A's-B's-C's space for cancer. (The mean derived values of A's, B's, and C's are the center locations.)

calculate the distances from all other data points to the center (of A's, B's, and C's) in the multi-dimensional space, and then compute the standard deviation, σ, for the distances from all data points to the center. This standard deviation can be used as a threshold to classify cancer and normal tissue.

In the classification phase, the present inventors first obtain the set of A's, B's, C's parameters to be identified, calculate the distance, R, to the center, P point, as determined in the training phase, given above, compute the normalized distance as $R_N=R/\sigma$ between the unknown data point and the center point, P, compare $R_N$ with the pre-defined threshold given in the training phase, and to classify the tissue.

The standard deviations are needed to be sufficient were determined. One might also reduce the parameter space to a lower dimension and demonstrate the classification accuracy for using fewer parameters.

Support Vectors Machine (SVM)

Mathematically, the classification function in SVM can be written as $f(x,\alpha)=\Sigma y_i \alpha_i K(x_i,x)+b$, where $\alpha_i$, b are model parameters and K is a kernel function. Given a set of N clinical data, which composed of input X (such as A's, B's, and C's in Section C3d) and output Y (−1 for normal tissue, +1 for cancer tissue), the parameters in the SVM are calculated to minimize the error from the SVM output and the known data while maximizing the margin between the two classes. This process is known as the training of SVM.

Once SVM is trained, it can be used to perform prediction. Given a set of measured parameters (x), the SVM classification is achieved by the following calculation: $Y(x)=\text{sign}(f(x,\alpha))$. Note that Y=−1 for normal tissue, Y=+1 for cancer tissue. While there are many classification schemes in the literature, SVM is chosen for this research for the following reasons: (1) SVM has a strong theoretical background, (2) SVM can be applied to large data set, (3) SVM algorithm is flexible, (4) SVM is very accurate and (5) SVM can be implemented in a silicon chip. The flexibility of SVM stems from the variety of choices of kernel functions, such as linear, polynomial, radial basis function (RBF) and Sigmoid function. Gaussian RBF is used in this research:

Gaussian: Radial Basis function (RBF): $K(x_i,x_j)=\exp(-\gamma\|x_i-x_j\|^2)$, $\gamma>0$.

Computationally, the training of SVM involves the solution of the quadratic programming (QP) problem:

$$\text{Minimize } \frac{1}{2}\sum_{i=1}^{N}\sum_{j=1}^{N} y_i y_j \alpha_i \alpha_j \left(K(x_i,x_j)+\frac{1}{C}\delta_{ij}\right) - \sum_{i=1}^{N}\alpha_i \quad \text{Equation (7)}$$

$$\text{Such that } \sum_{i=1}^{N}\alpha_i y_i = 0, \alpha_i \geq 0, i=1,\ldots,N$$

The support vector output is $$f(x) = \sum_{i=1}^{N} y_i \alpha_i K(x_i,x)+b.$$

Human Kidney Measurements During Laparoscopic Surgery

Human measurements were conducted in the operating room using the newly developed positive cancer margin detection system (spectroscopic system and laparoscopic probe combination). Subsequently the classification algorithms were applied to these measurements to demonstrate the technique's ability of identifying kidney cancer.

The newly constructed probe were used during human laparoscopic nephrectomy (n=14). When the kidney cancer resection is complete, the probe was inserted through the laparoscopic ports and rested on the surgical margin. Spectroscopic measurements (optical and NIR reflectance and autofluorescence lifetime) were recorded and stored for later analysis. Several spectra per modality were taken in each data-collection site with a few millimeters apart and across the whole resection margin. Spectroscopic measurements were analyzed by the classification algorithms. Success was defined as having a greater than 90% rate of correct tissue identification. Should one cannot correctly identify kidney cancer with that level of specificity, the observed data are subjected to re-analysis by computational modeling tools with a focus on data points in the margins between tissue classes, in order to develop an updated classification scheme. Following this adjustment, the probe was demonstrated on another 15 human patients. Multiple readings were obtained (n=5) and tested in humans to determine reproducibility. After the laparoscopic measurements have been completed, spectroscopic measurements were performed on the freshly excised samples. The latter are an important part of the classification algorithm training process as these permit direct comparison with histology.

During the surgery, by the time when the human kidney specimen is just completely resected, the probe was inserted through the laparoscopic ports and rested on the resected specimen. Several spectra were taken in each data-collection site with a few millimeters apart. To confirm the landmarks, some surgical staplers on the resected specimen may also be used.

The optical spectra were subjected to the classification program. Success was defined as having a greater than 90% rate of correct tissue identification. Should one not be able to correctly identify the cancer, the observed optical spectra are subjected to re-analysis by the mathematical modeling algorithms to develop an updated classification scheme specific for human kidney tissues. Following this adjustment, the probe are tested on another group of human patients. Multiple readings were be obtained (n=5) and tested in humans to determine reproducibility. Correct tissue identification at a 90% rate are the acceptable limit for the probes.

Statistical Methods

A student-t test was used to determine those parameters that are significantly altered from the normal tissues. Cross-correlations were studied to determine causal, complementary, parallel, or reciprocal relationship, especially a structural, functional, or qualitative correspondence between the spectroscopic modalities and surrogate markers within each modality. Furthermore, ANOVA (Analysis of Variance) were applied to conduct comparisons among the modalities and surrogate markers within each modality.

Example

Prostate Cancer

The present invention aims to develop a tri-modal optical spectroscopic approach that integrates three different techniques: light-scattering reflectance, time-resolved fluorescence, and diffuse near infrared spectroscopy (NIRS). The overall goal is that tri-modal optical spectroscopy (i.e. light-scattering reflectance, time-resolved auto-fluorescence and near infrared spectroscopy) enables surgeons to intraoperatively demarcate prostate cancer over the entire resected prostate so as to significantly reduce positive surgical margins and prostate cancer recurrence after surgery.

Near Infrared Spectroscopy (NIRS) and Optical Properties of Human Prostate: In spite of a significant amount of work have been conducted to quantify the optical and physiological properties of human breast and breast cancer using the non-invasive NIRS approach, limited information is available for the optical parameters of human prostate. With the help of MRI, it was reported that 9 out of 30 cases do not show close correlation between the optical density and the presence of prostate cancer, and that prostate cancers do not consistently respond to oxygen intervention, namely not exhibiting the characteristic of high vascular density. It was recently suggested using water absorption as a possible marker for prostate cancer diagnosis and integrating spectral polarization with an NIR receptor-targeted contrast agent to enhance cancer detection. However, due to the lack of sufficient studies on healthy and diseased human prostates, the present inventors that it is too early to exclude the roles that hemoglobin concentrations (i.e., deoxy-, oxy-, and total hemoglobin) and oxygen saturation play as possible diagnostic markers for human prostate cancer.

The data shown here strongly demonstrate that light scattering and water concentration are clearly distinct between healthy and cancer prostate tissues taken from animal models in vivo and human prostates ex vivo.

Most of the techniques developed for in vivo cancer detections mainly target luminal malignancies, such as cervical, colon, and esophageal cancers. Prostate cancer, on the other hand, is an intraparenchymal tumor that is commonly multifocal. For early clinically localized disease, the most common presentation, it is not possible to visually identify the prostate cancer during surgery, either within the prostate or at its capsular margin (5-30% of cases). This is the reason for the development of the present invention that allows the surgeons in real time to detect prostate adenocarcinoma both on the surface of the prostate and a few millimeters beneath the surface for accurate excision of the cancer during laparoscopic prostatectomy.

The novelty of the present invention includes (I) tri-modal integration of optical spectroscopy to identify positive surgical margins (PSM) of prostate cancer in vivo during laparoscopic prostatectomy and (II) novel classification algorithms for the Identification of PSM. Regarding I, here the difference are present in that the difference being that (a) prostate adenocarcinoma was targeted both on the surface of the prostate and a few millimeters beneath the surface, and (b) the intrinsic fluorescence lifetimes of prostate cancer as a potential marker for cancer demarcation was determined. The tri-modal integration provides a robust approach to this biomedical engineering problem facilitating a higher likelihood of success. Regarding II, cancer versus healthy tissue shown during prostatectomy must be rapidly classified as corresponding to the unique tissue for this technology to be clinically useful. Two particular classification algorithms were used to identify prostate cancer: (a) the minimal distance method and (b) the support vector machine (SVM), a newer technique used for machine learning and ideal for data classification.

To obtain preliminary spectroscopic data from the human prostate glands immediately after prostatectomy, 3 different setups was used for reflectance spectroscopy and steady-state fluorescence measurements: 3-channel diffuse (NIR) light reflectance measurement was performed with a hand-held probe having source-detector separations of 0.9, 1.5, and 2.2 cm (FIG. 17a); a single-channel spectrometer FIG. 17(b) was used for light-scattering reflectance spectroscopy with a needle-like probe having a source-detector separation of 0.5 mm (seen in FIG. 17c). The same spectrometer was used along with a UV light source and a cut-off filter at 400 nm (to filter out the UV excitation) for steady-state fluorescence spectroscopy. For the single- and multi-channel spectrometers, the wavelength regions were 350-1100 nm and 350-900 nm, respectively.

Figure 17:
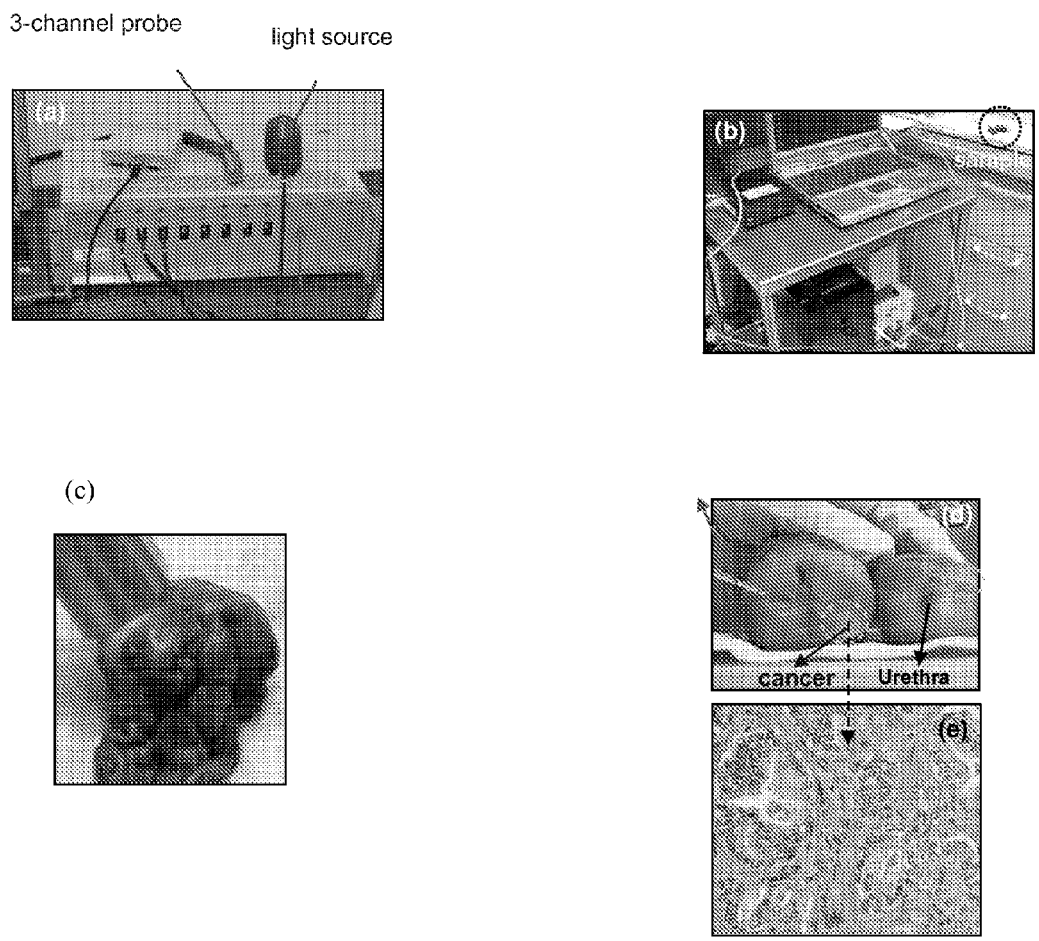
FIG. 17(a) is a picture showing a diffuse near infrared reflectance spectroscopy with 3 different source-detector separations integrated within a 3-channel probe.
FIG. 17(b) is a picture showing single-channel spectrometer used for both light-scattering reflectance and steady-state fluorescence measurements. In this case, the source-detector separation is ~0.4 mm.
FIG. 17(c) is a picture showing the relative locations of both single- and multi-channel probes with respect to a resected prostate gland when the optical readings were taken on the surface of the resected prostate.
FIG. 17(d) is a picture showing one placement of the single-channel probe when it reads either the light-scattering reflectance or steady-state fluorescence after the resected prostate was bivalved.
FIG. 17(e) is a picture of a pathology image.

FIG. 17 shows spectrometer-based setups: (a) diffuse near infrared reflectance spectroscopy with 3 different source-detector separations integrated within a 3-channel probe; (b) single-channel spectrometer used for both light-scattering reflectance and steady-state fluorescence measurements. In this case, the source-detector separation is ~0.4 mm. (c) It shows the relative locations of both single- and multi-channel probes with respect to a resected prostate gland when the optical readings were taken on the surface of the resected prostate. (d) It shows one placement of the single-channel probe when it reads either the light-scattering reflectance or steady-state fluorescence after the resected prostate was bivalved. (e) It is a pathology image (with a magnification of ×10 objective field) taken from a cancerous area, as labeled by a circle in (d).

Multi- and single-channel probes/spectrometers was used to measure the light reflectance from the surface of the intact resected prostate (FIG. 17c) to obtain the optical signatures under such a condition. However, to locate the prostate cancer, the prostate gland was bivalved for pathology analysis. Before fixing the prostate specimen, both light scattering and steady-state auto-fluorescence spectra were taken at multiple locations of the bivalved cross section (FIG. 17d). In some cases, prostate adenocarcinoma can be visually identified by the pathologist in several scattered small areas, as circled in FIG. 17d. Confirmation of cancer came from the final pathology report, and FIG. 17e shows an example of irregular glands and clumps of cells, characteristic of prostate adenocarcinoma. Using the pathology report, the light reflectance and auto-fluorescence data were compared and characterized, and a few examples are given below.

Light Scattering Reflectance from Ex Vivo Human Prostate

Figure 18:
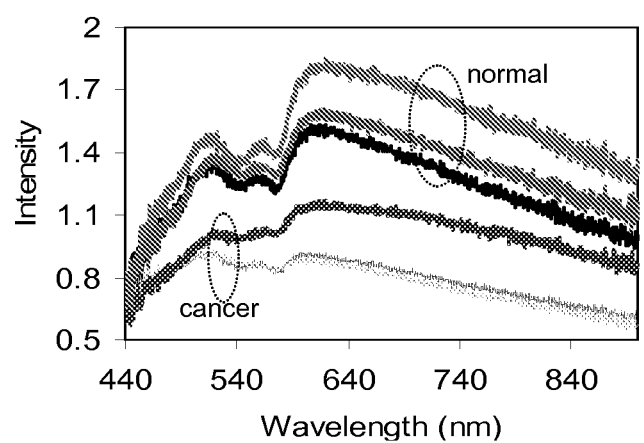
FIG. 18 is a plot of light scattering reflectance of human prostate.

FIG. 18 shows a few light scattering reflectance spectra taken from the bi-valved prostate cross section using the needle-like probe (FIG. 17d). The curves were calibrated with a white standard reflectance sample. After confirming with the pathology report, the top three spectra in FIG. 18 were recognized originated from healthy prostate gland areas and the bottom three from cancerous ones.

Figure 19:
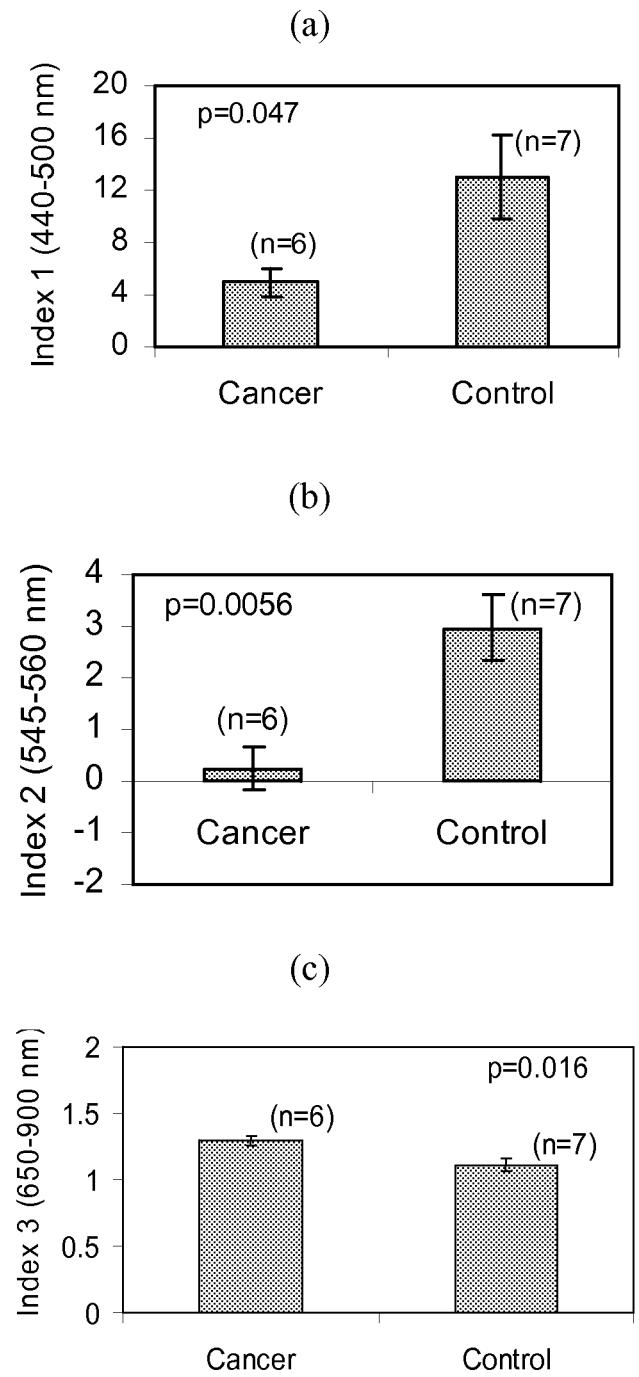
FIGS. 19(a)-19(c) are plots showing statistical analysis of three calculated slopes at 440-500 nm, 545-560 nm and 650-900 nm.

With multiple resected prostate glands measured and multiple sites used, three particular spectral ranges were selected: 440-500 nm, 545-560 nm, and 650-900 nm for data analysis to determine possible markers to distinguish prostate adenocarcinoma from normal gland tissues. Within those three ranges, the present inventors used spectral slopes as indexes for comparison. FIG. 19 shows an example taken from one prostate gland. Statistical analysis of three calculated slopes, i.e., indexes, (a) at 440-500 nm (index 1), (b) 545-560 nm (index 2) and (c) 650-900 nm (index 3) between prostate cancer and normal tissues. The values of "n" represent the number of measurement sites for this particular prostate gland; error bars are based on SEM.

Figure 20:
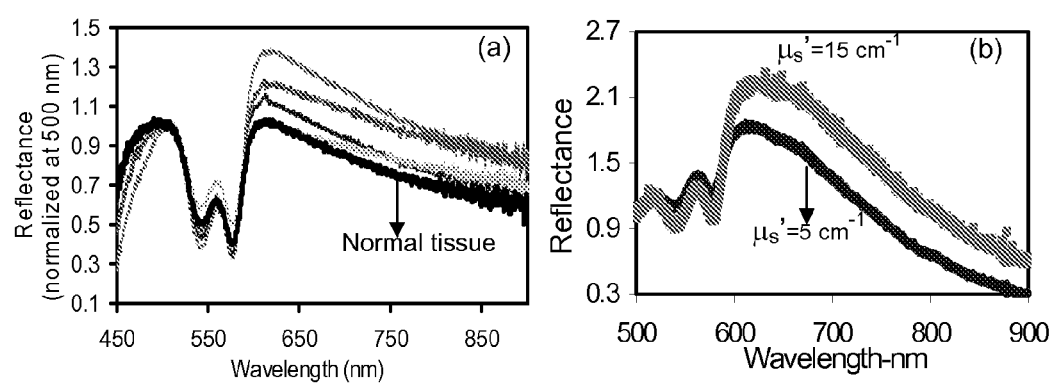
FIG. 20(a) is a plot of calibrated and normalized light scattering reflectance spectra taken from the surface of an intact resected prostate gland, only one spectrum being taken from the normal tissue (black curve)
FIG. 20(b) is a plot of lood-intralipid tissue phantom data taken with two reduced light scattering coefficients: namely, $\mu_s'=5$ (in blue), $\mu_s'=15$ cm$^{-1}$ (in pink)

On the other hand, it is also important to know the spectral shapes of the light-scattering reflectance spectra obtained with the needle-probe from the prostate capsule surface (FIG. 17c). FIG. 20a below shows several spectra taken under such a condition from the cancer and normal areas. All the curves are calibrated and normalized at 500 nm. Among all 5 spectra, only the thick black curve was taken from the normal area, but all the other 4 curves were taken from cancerous areas. Besides the common absorption feature of oxygenated hemoglobin at 500-600 nm, the present inventors noticed that all the spectra taken from the cancerous areas have higher light reflectance in the region of 600-900 nm. This results from an increase in light scattering in the region of 450-900 nm. To confirm this, two blood-intralipid tissue phantoms were created with two different scattering coefficients while keeping the same amount of hemoglobin concentration and oxygen saturation. FIG. 20b plots the data that were calibrated and normalized as FIG. 20a. It proves that a higher scattering medium exhibits a larger light reflectance spectrum. The increase in light scattering seen in FIG. 20a result from the enlarged cell nuclei and increased cell densities that are often encountered in prostate cancer tissues.

A recent theoretical development in light scattering is and further affords to quantify the optical properties of the measured sample using the light reflectance spectra. The present inventors used this analytical expression for light reflectance to recover the optical and physiological parameters of the prostate adenocarcinoma in both ex vivo and in vivo studies.

Auto-Fluorescence from Ex Vivo Human Prostate

Using a similar needle probe to the one used for the reflectance readings, auto-fluorescence were measured from the bi-valved prostate cross section (FIG. 17d). The fluorescence excitation source was a broadband UV lamp with a cut-off filter at 400 nm that was placed in front of the lamp, so only 400 nm and shorter wavelengths can be delivered to the prostate specimen. The UV light was collimated and delivered to a bifurcated 1-mm fiber probe tip, and the detected auto-fluorescence was collected and sent to the single-channel spectrometer (FIG. 17b). While the detected spectral range was 350-1100 nm, The present invention focused on the UV-visible region, where NADH has a strong auto-fluorescence peak (at 460 nm). This portable fluorescence measurement system (FIG. 17b) was calibrated against a standard laboratory fluorometer before processing the ex vivo prostate data.

Figure 21:
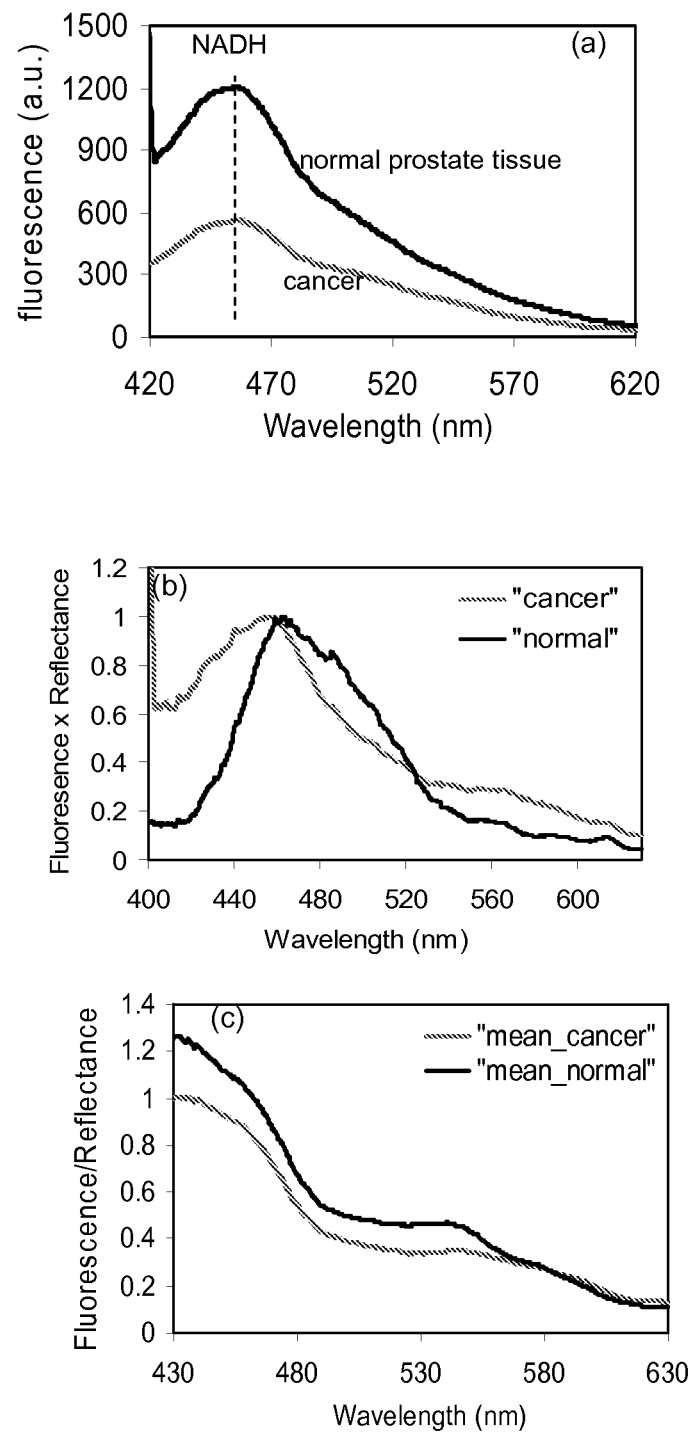
FIG. 21(a) is a plot showing auto-fluorescence spectra from a cancerous (pink curve) and normal tissue (black curve) region of a bi-valved prostate cross section. The main peaks are at 460 nm due to fluorescence from NADH.
FIG. 21(b) is a plot showing normalized product spectra of autofluorescence and light scattering reflectance: pink curve is for cancer and black curve for normal tissue.
FIG. 21(c) is a plot showing ratio spectra between autofluorescence and scattering reflectance (pink for cancer)

FIG. 21a shows two calibrated, steady-state autofluorescence spectra taken from a region of cancer and normal prostate gland, exhibiting a strong peak at 460 nm due to NADH. However, the two curves differ only in amplitude, no other distinct aspects between them. Then, the autofluorescence signals were combined with the scattering reflectance (given in FIG. 20a) by either multiplying them (FIG. 21b) or dividing the fluorescence by the reflectance (FIG. 21c).

NIRS Taken from Ex Vivo Human Prostate

Figure 22:
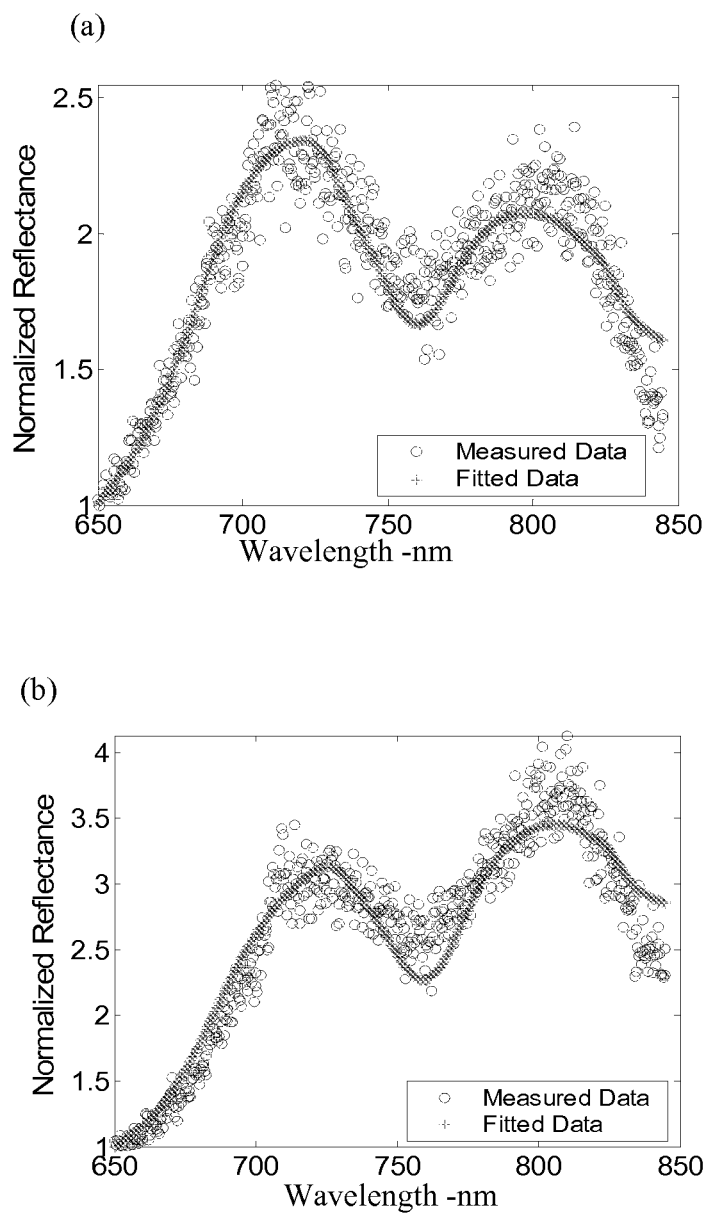
FIGS. 22(a)-22(b) are plots showing comparison of reflectance spectra in the NIR region taken from normal and cancerous areas on a resected human prostate with their respective diffusion theory fits.

FIGS. 22a and 22b are the diffuse reflectance spectra taken from an intact resected prostate gland ex vivo using the multi-channel, large source-detector separation probe (see FIGS. 17a and 17c). The blue dotted symbols refer to the measured data, and the solid red lines are their respective diffusion theory fits. The diffusion-theory-based, spectrum-fitting algorithm has been very recently developed using water absorption as a reference to obtain initial fitting conditions. The data shown in this example were made with a separation of 1.5 cm. Specifically, FIG. 21a was obtained on the region that was devoid of any possible tumors on/near the surface, while FIG. 21b was made from the region as possible tumors indicated by the surgeon and pathologist. The fitted physiological and optical parameters are oxy-, deoxy-, total hemoglobin concentrations, water concentrations, and reduced light scattering coefficients ($\mu_s'$) from both regions, and those parameters are listed in the following Table 3.

TABLE 3

| 1.5 cm Separation | [HbO] μM | [Hb] μM | [HbT] μM | % H$_2$O | $\mu_s'$ (at 700 nm) cm$^{-1}$ |
|---|---|---|---|---|---|
| Tumor Regions (n = 5) | 34 ± 7 | 34 ± 3 | 68 ± 10 | 68 ± 2 | 11.5 ± 0.7 |
| Non-Tumor Regions (n = 29) | 38 ± 3 | 26 ± 3 | 64 ± 5 | 72 ± 1 | 11 ± 0.7 |

The data given in the Table 3 are expressed in mean SEM (standard error of mean). While more statistical analysis is needed to draw a reliable conclusion, it is seen primarily that the tumor regions have higher total and deoxy-hemoglobin, lower oxy-hemoglobin and water concentrations, perhaps larger light scattering, as expected and consistent with the reported literature for the prostate tumors.

Figure 23:
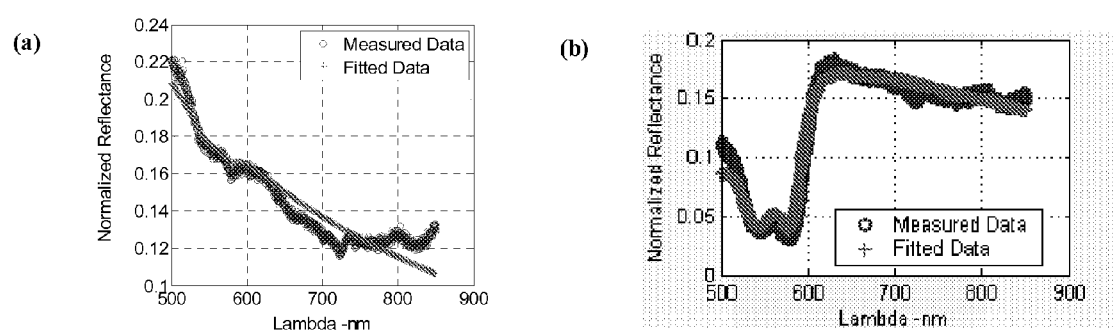
FIGS. 23(a)-23(b) are plots showing a comparison between the measured (blue symbols) and fitted (red curve) spectra, taken internally from a bi-valved region, which do not show strong hemoglobin features between 500-600 nm, whereas (b) is obtained externally from an intact excised human prostate with both measured and fitted data.

Quantification of Physiological Parameters of Human Prostate Glands from the Light Reflectance Measurements The algorithm to quantify optical and physiological parameters of the human prostate gland was developed using the reflectance spectra taken from the small source-detector probe. Using the light reflectance mode, the present inventors were able to fit the model to the light reflectance so as to quantify concentrations of oxygenated and deoxygenated hemoglobin, concentration of melanin, reduced light scattering coefficient at 450 nm, averaged light scattering size, and water concentration of the local measured area from the human prostate. FIG. 23a shows a comparison between the measured (blue symbols) and fitted (red curve) spectra, taken internally from a bi-valved region, which do not show strong hemoglobin features between 500-600 nm, whereas FIG. 23b is obtained externally from an intact excised human prostate with both measured and fitted data. The latter case exhibits a strong absorption dip due to hemoglobin existence. The table 4 below lists all the fitted parameters obtained from the model curve fitting, showing that the optical and physiological parameters can be largely varied between the measurements obtained externally (FIG. 23b) and internally (FIG. 23a) from the same human prostate gland.

TABLE 4

| | HbO (micro Molar) | Hb (micro Molar) | Oxygen hemoglobin saturation (%) | Melanin (micro Molar) | Scattering parameter at 450 nm (cm$^{-1}$) | Average Scattering Diameter (micron) | Water (%) |
|---|---|---|---|---|---|---|---|
| FIG. 23a readings | 0.94 | 2.1 | 30.9 | 0.81 | 15.0 | 0.95 | 0.78 |
| FIG. 23b readings | 59.0 | 17.5 | 77.1 | 0.01 | 7.6 | 0.48 | 0.82 |

Figure 24:
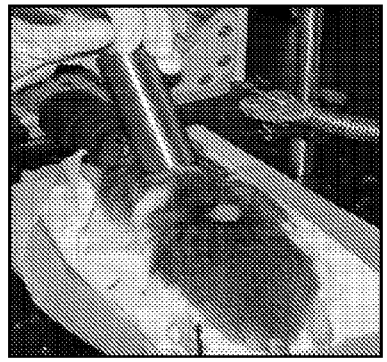
FIG. 24(a)-24(b) are pictures showing a male tumor-bearing Copenhagen rat with the large-separation probe sitting on top of the prostate tumor with an exposed living prostate tumor on the rat fore back.
FIG. 24(c)-24(d) are plots showing steady-state autofluorescence and light-scattering reflectance were taken from the exposed rat tumor to avoid the skin effect.
Figure 24:
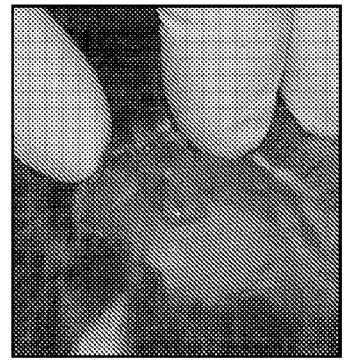
Figure 24:
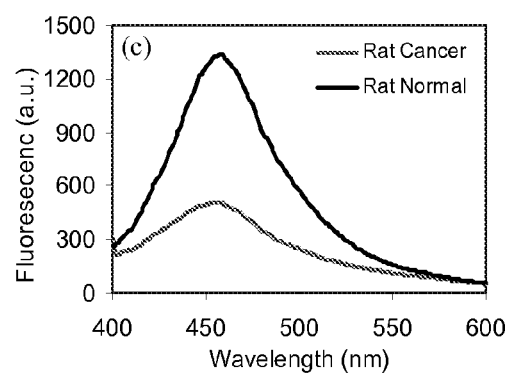
Figure 24:
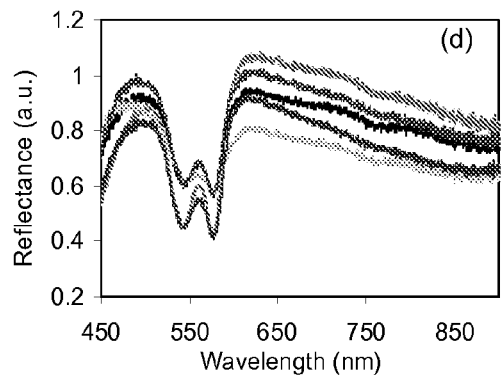

Light-Scattering Reflectance and Auto-Fluorescence from Rat Prostate Tumor In Vivo The present inventors also have developed a rat prostate tumor model, using adult male Copenhagen rats that were implanted with prostate carcinoma on the fore back (FIGS. 24a and 24b). Animal tumors of light scattering reflectance (FIG. 24d) and autofluorescence (FIG. 24c) using the needle-like probe, as well as the diffuse light reflectance with the multi-channel probe. By comparing FIGS. 21a and 24c, also FIGS. 20a and 24d, The present inventors noticed that the data from the human prostate tumor are very consistent with those taken from the rat tumor, and this conclusion holds for both light scattering reflectance and autofluorescence.

Auto-Fluorescence Lifetime of Rat Prostate Tumor Measured In Vitro

The present inventors have applied the time-resolved technique to demonstrate the auto fluorescence lifetime of the rat prostate tumor tissues compared to the normal muscle tissues. Both types of tissues were removed from the rats a few hours before the measurements. The main advantage of the time-resolved fluorescence is that such measurements reveal intrinsic fluorophore photophysics parameters, which are intensity independent. For these measurements, a Fluo-Time200 fluorometer was used equipped with pulsed light sources. The excitation of 375 nm hoping for efficient NADH/Flavins excitation were selected.

The demonstration detected strong fluorescence signals in the visible region of 440-550 nm. The present inventors also attenuate the signal by 100 fold using a neutral density filter with OD=2, and still collect high quality lifetime data. Thus, one would not expect any problem with the autofluorescence data collection in future time-resolved "Field" measurements in vivo.

Figure 25:
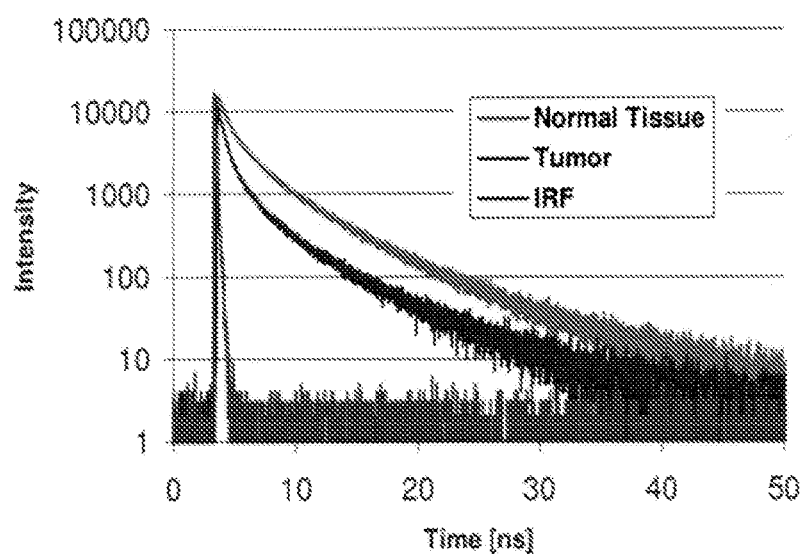
FIG. 25 is a plot showing time-resolved auto-fluorescence data from both rat tumor and normal tissues.

An example of the time-resolved tissue autofluorescence is presented in FIG. 25, where the red and black curves result from the normal and prostate tumor tissues, respectively. The blue sharp spike is the instrument response function. This figure clearly shows a significant lifetime decrease in tumor tissue. The autofluorescence intensity decays of the tissue can be approximated with the multi-exponential model, as given:

$$I(t) = \Sigma \alpha_i \exp(-t/\tau_i) \quad (8)$$

where $\tau_i$ are the decay times, $\alpha_i$ represent the amplitudes of the components at t=0. In this case, three components (n=3) were sufficient to fit the data with an acceptable confidence. The fractional contributions $f_i$ of each decay time to the steady-state intensity is given by $$f_i = \alpha_i \tau_i / \Sigma \alpha_j \tau_j. \quad (9)$$

Then, the average lifetime for multi-exponential decay is given by $\tau = \Sigma f_i \tau_i$. Another quantity, called amplitude-weighted lifetime, is given by $\langle \tau \rangle = \Sigma \alpha_i \tau_i$, which is proportional to the area under the curve.

The following Table 5 provides a list of lifetime parameters analyzed using eqs. (8) and (9).

and prostate tumor tissue. This knowledge implies that both $\langle \tau \rangle$ and $\tau$ may be used as classification markers to identify prostate tumor from normal tissues. In short, this time-resolved demonstration shows that decays in autofluorescence intensity from prostate cancer are easily detectable, and that time-resolved autofluorescence of the tissue is durable, carrying characteristic information on cancer.

NIRS of Rat Prostate Tumor In Vivo

Figure 26:
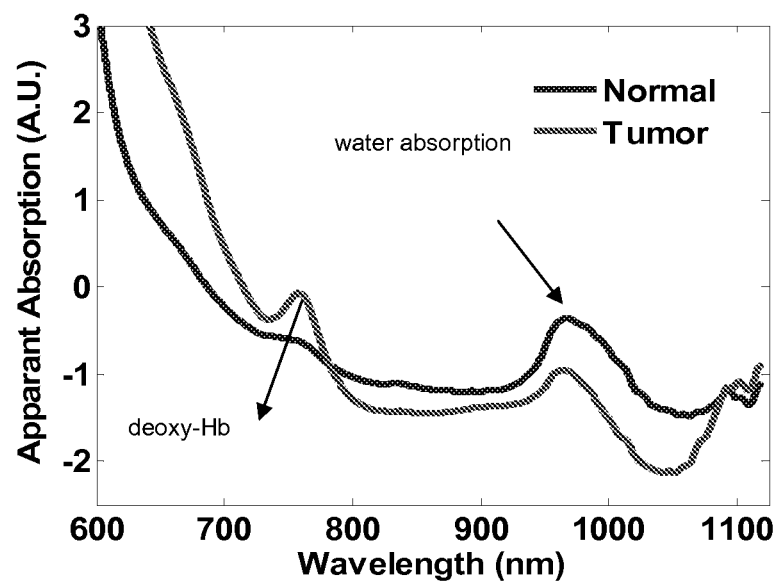
FIG. 26 is a plot showing log of reciprocal reflectance.

The animal demonstration data are very consistent with the human prostate cancer for both light reflectance and autofluorescence. Indeed, the diffuse NIR reflectance from the rat tumor displayed NIR spectra similar to FIG. 22a. Moreover, the data was inspected in the NIR region up to 1100 nm so as to examine the signals at dominant water absorption. FIG. 26 plots apparent absorption, which is calculated by taking the logarithm of reciprocal reflectance. This result clearly demonstrates that the prostate tumor has lower water and higher deoxy-hemoglobin concentrations than normal tissues.

Classification Algorithms to Demarcate Prostate Cancer

The Minimal Distance Method (MDM) is a statistical matching process commonly used in pattern recognition for remote sensing and image processing. Class assignment follows minimization of the Euclidan (linear) or Mahalanobis (correlated) distance. It was found that Mahalanobis distance to be useful being that it is scale-invariant and accounts for correlations within data sets. Furthermore, the Support Vectors Machine (SVM) has found great utility in machine learning. It is a supervised learning algorithm that recognizes subtle patterns contained in complex data sets. SVM is an effective classifier, and has been used with increasing frequency in recent years.

Figure 13:
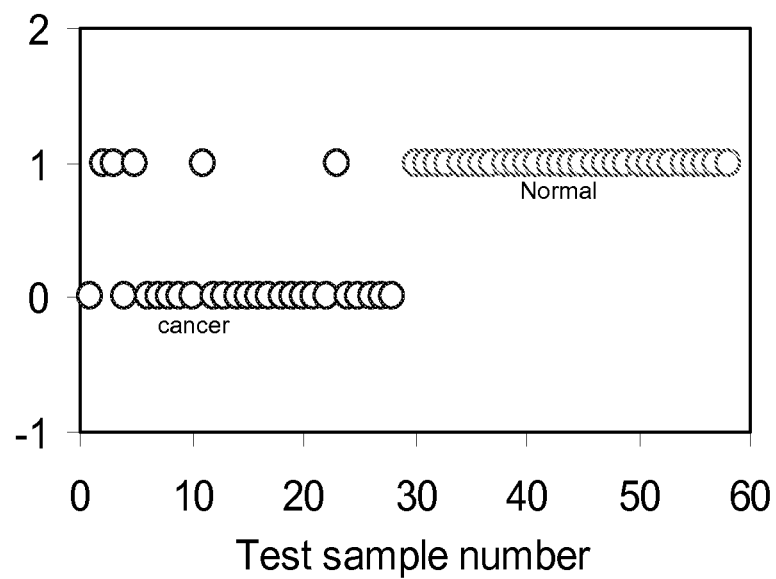
FIG. 13(a) is a plot of demonstration of classification for cancer and normal tissue using the SVM method.
FIG. 13(b) is a plot of summary of success rates using different number of parameters chosen from A's and B's. "para"=parameter.
Figure 13:
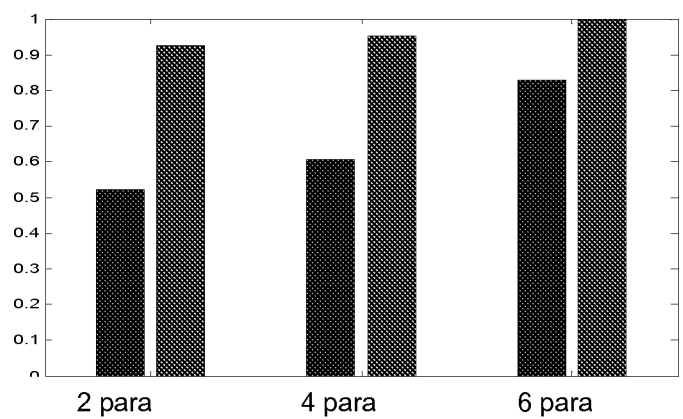

Similar to FIG. 13 in Kidney cancer example, MDM and SVM were used as classification algorithm. In parameter selections, 10 parameters were picked up that were derived from light-scattering reflectance, autofluorescence lifetime, and diffuse NIR reflectance. These parameters are Index 1, index 2, index 3, $\langle \tau \rangle$, $\tau$, HbO, Hb, HbT, $\mu_s'$, and water concentration, labeled A1, A2, A3, B1, B2, C1, C2, C3, C4, and C5, respectively. In the simulated classification runs, 240 uniformed distributed sample points were generated for each of A's, B's and C's with a uniformly distributed random numbers in the range of mean±S.D. For each set, 211 points were used to train the classifiers, and the rest 29 samples for each set were available for testing the performance of the classification algorithms. Next, 3 or 5 parameters were randomly selected (such as A1, A2, C1, C3, and C5) out of the 10 parameters to determine classification success rates in comparison to the rate with all 10 parameters used.

Methods

Figure 27:
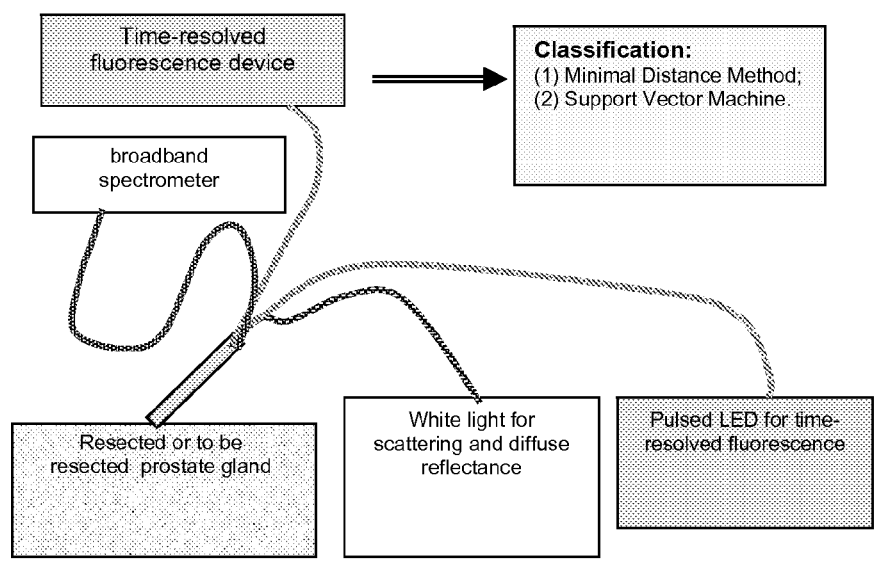
FIG. 27 is a schematic for the setup in the prostate cancer demonstration.

FIG. 27 shows the overall tri-modal detection system design: 1) intra-operative probe, 2) multi-channel spectrometer, 3) time-resolved technique for measuring fluorescence lifetime, and 4) classification algorithms for the identification of prostate adenocarcinoma.

TABLE 5

| Observation (465 nm) | $\alpha_1$ | $\tau_1$ (ns) | $\alpha_2$ | $\tau_2$ (ns) | $\alpha_3$ | $\tau_3$ (ns) | $\langle \tau \rangle$ (ns) | $\tau$ (ns) | $\chi_R^2$ |
|---|---|---|---|---|---|---|---|---|---|
| Normal | 0.62 | 0.53 | 0.30 | 2.22 | 0.08 | 6.52 | 1.53[a] | 3.36[b] | 1.19 |
| Tumor | 0.73 | 0.35 | 0.22 | 1.51 | 0.05 | 5.83 | 0.86 | 2.49 | 1.01 |

[a] $\langle \tau \rangle = \Sigma \alpha_i \tau_i$;
[b] $\tau$ is the average lifetime and equal to $\Sigma f_i \tau_i$, $f_i = (\alpha_i \tau_i)/(\Sigma \alpha_i \tau_i)$ This table unambiguously demonstrates that both amplitude weighted lifetime and average lifetime, i.e., $\langle \tau \rangle$ and $\tau$, are significantly different between the normal muscle tissue Measurements Taken on Ex Vivo Human Prostate Specimens Using existing spectroscopic system, one can measure light-scattering reflectance and diffuse NIR reflectance, using both needle-like and multi-channel probes for ex vivo human prostate glands. In particular, the measurements take place immediately (10 minutes or less) after the prostatectomy so that the tissues have not been denatured too much. Also, one can perform the measurements before and after bi-valving the resected human prostate to obtain the optical signatures on and under the prostate capsule. quantify spectral features of light scattering reflectance, as well as to quantify oxygenated (HbO), deoxygenated (Hb), total hemoglobin (HbT), water concentration ($H_2O$), and reduced light scattering coefficient ($\mu_s$) for both internal and external areas.

Histologic maps of cancer distribution were obtained at different locations and depths, as a gold standard to validate the optical parameters for prostate adenocarcinoma classification. Upon the availability of histological analysis, the present inventors were able to determine the distinct characteristics in all selected parameters, including Hb, HbO, HbT, H2O, and $\mu_s'$, between normal and cancerous prostate tissues.

Implementation of a Multi-Channel, Dual-Modal Spectrometer

Figure 28:
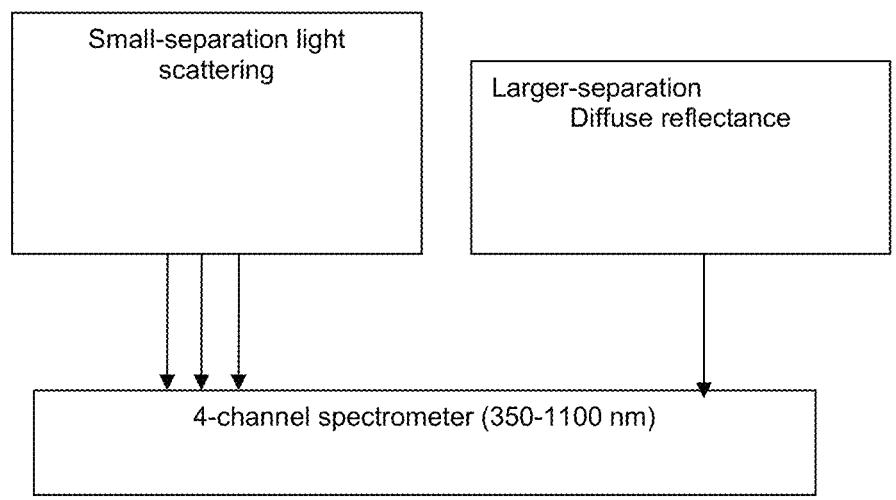
FIG. 28 is a schematic diagram illustrating the setup protocol in the prostate cancer demonstration.

The present inventors implemented a multi-channel spectrometer in a similar format as shown in FIG. 1a. Four channels of Ocean optics' HRD-4000, which has 16-bit dynamic range and a wavelength region of 350-1100 nm was used. 3 channels were available to record light-scattering reflectance signals and 1 channel for diffuse NIRS reflectance signal were used. The information for the detailed probe design is given below and in FIG. 28. The first three small-separation (~400 µm) channels for light scattering reflectance to detect the area on the prostate capsule within 1 mm depth, while the diffuse NIRS channel enables the present inventors to sense a few millimeters deep under the capsule. In this way, it enables one to interrogate a larger prostate tissue volume and obtain their spectroscopic features for cancer classification. A schematic diagram is shown in FIG. 28.

Design and Build an Intraoperative NIR Probe

Figure 29:
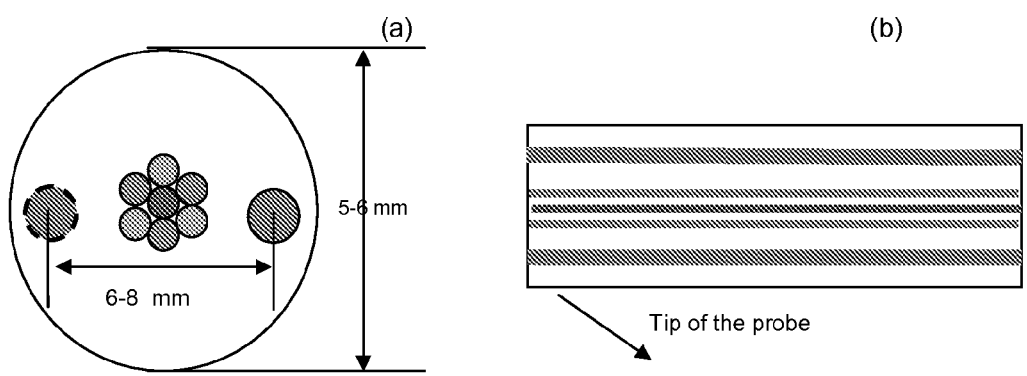
FIG. 29 is a picture showing the optic fiber used in the prostate cancer embodiment.

Since this demonstration is to integrate three modalities for intraoperative classification of prostate adenocarcinoma, it was needed to design a unified probe that can collect all the information as shown in FIG. 29. The overall outer diameter is about ~1 cm (not more than 1 cm), which is compatible with the ports for laparoscopic prostatectomy. The probe is rigid and is about 25-30 cm in length, to be compatible with the surgery. In one embodiment, there are 9 fibers included inside the probe, and FIG. 29a shows a cross section. The 7 fibers at the center are 400 µm in diameter, and the center fiber (red) surrounded by the other six are be used to deliver the white light, coming from a Tungsten-Halogen light source. Three out of six surrounding fibers (blue) are connected to the multi-channel spectrometer for light-scattering reflectance measurements. The other three (gray) fibers are used for the time-resolved auto-fluorescence measurements, although only two are needed. One extra channel can be used for other purposes. The two far-apart fibers are to be used for the diffuse NIR reflectance measurement.

Implementation of Time-Resolved Fluorescence Device

Figure 30:
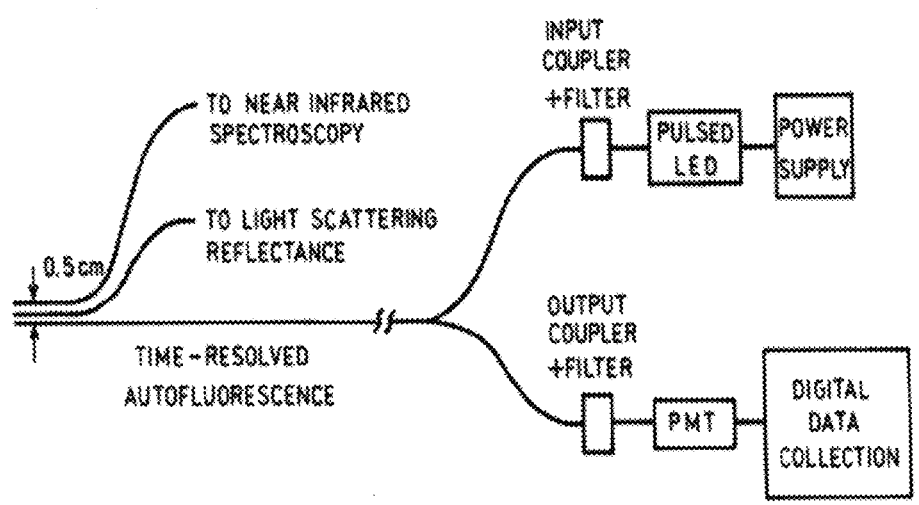
FIG. 30 is a schematic diagram showing a time-resolved path of integrated TMOS.

FIG. 30 shows a time-resolved path of integrated TMOS, a proposed laparoscopic probe for prostate condition evaluation. The time-resolved device are portable and easily fit to the movable cart, similar to the other two modals. The light excitation source is a pulsed, 370 nm light emitting diode (LED), which is powered by a signal generator driver at 40 MHz frequency. The pulse width of this LED is about 400 ps. On the detection path, an inexpensive photomultiplier was used, PMT (Hamamatsu, R928), operating with a high voltage power supply. The detected signal are processed by a digital acquisition card, controlled by a PC computer. The temporal resolution of this portable time-resolved device is about 150 ps, which is adequate to observe small changes in the tissue lifetime. The sensitivity in the single-photon counting mode is superior to other techniques used for the lifetime measurements. The lifetime measurements are fast and reliable, because they are excitation intensity independent. Just recently, the costs of crucial elements for the construction of time-resolved measurements have been lowered, making this technique more attractive.

Algorithms to Determine Physiological Parameters a Few Millimeters Below the Tissue Surface For diffuse NIR reflectance, The combine diffusion theory and spectroscopic approach were taken to analyze the steady-state diffuse reflectance, R, where R is the diffuse photon flux escaping from the tissue/boundary interface (i.e., at z=0). The reflectance can be measured through the NIRS reflectance and is written as 'R'

$$R(\rho, z_0) = \frac{I_0}{4\pi}\left[z_0\left(\mu_{eff} + \frac{1}{r_1}\right)\frac{\exp(-\mu_{eff}r_1)}{r_1^2} + (z_0 + 4AD) \times \left(\mu_{eff} + \frac{1}{r_2}\right)\frac{\exp(-\mu_{eff}r_2)}{r_2^2}\right] \quad (10)$$

In the diffusion regime ($\mu_a \ll \mu_s'$), equation (10) has been shown in good consistency with spatially resolved Monte Carlo simulations. Since the spectral dependence of absorption ($\mu_a$) for blood-perfused tissues can be written as:

$$\mu_a(\lambda) = HbO^* \epsilon_{HbO}(\lambda) + Hb^* \epsilon_{Hb}(\lambda) + \epsilon_{H2O}(\lambda) H_2O \quad (11)$$

where $\lambda$ is wavelength in nm, HbO, Hb, $H_2O$ represent concentrations of oxy-, deoxy-hemoglobin, and water respectively, and $\epsilon_{HbO}(\lambda)$, $\epsilon_{Hb}(\lambda)$, $\epsilon_{H2O}(\lambda)$ are extinction coefficients for HbO, Hb, and $H_2O$ at $\lambda$, respectively. Moreover, it is known that the spectral dependence of light scattering ($\mu_s'$) of tissue is weak and can be approximated as the following equation $$\mu_s'(\lambda) = a_s \lambda^{-p_s} \quad (12)$$

where $a_s$ and $p_s$ are light scattering amplitude and power. By substituting equations (11) and (12) into equation (10), a quantitative relationship was obtained between the parameters of Hb, HbO, $H_2O$, $a_s$, $p_s$ and the measured light reflectance from the NIR multispectral images in the wavelength range of 600 nm to 1100 nm. This set of parameters (i.e., Hb, HbO, $H_2O$, $a_s$, $p_s$) can be obtained by fitting the equation with the data, resulting in the final quantification of HbO, Hb, HbT, hemoglobin oxygen saturation, ($SO_2$), light scattering amplitude, $a_s$, and scattering power, $p_s$. This approach to quantify all Hb, HbO, and light scattering coefficients has been also proved by several groups.

For small-separation light reflectance, the newly developed theoretical expression was used to fit the data, which permit quantitative calculations of Hb, HbO, $H_2O$, and light scattering coefficient.

Laboratory Phantoms

To demonstrate the tri-modal spectroscopic system with the probe, the present inventors utilize a tissue phantom consisting of a blood-lipid complex. A laboratory phantom was built, consisting of a liquid mix of blood, lipid, and fluorescence dye, all of which is surrounded by a thin layer. The emission wavelength of fluorescence dye is around 460 nm. The phantom has a size of 3-4 cm diameter and 2-3 cm in height. It can be oxygenated or deoxygenated by bubbling oxygen or nitrogen gas into the covered phantom so that the parameters of oxy-, deoxy-, and total hemoglobin concentrations can be varied for system demonstrating and validation. By changing intralipid concentrations in the phantom, one can vary light scattering properties for $\mu_s'$ quantification.

For the outer layer, a colored plastic sheet was used and examine if it is sufficient to mimic the prostate capsule. The layer thickness should be around 1-2 mm. To do so, the present inventors used VeriSiTal (VST) silicone elastomers, a new concept in silicone technology. This elastomer is a 2-component type elastomer consisting of a Base (Part A) and a Catalyst (Part B) with a cure time RTV of 24 hours.

Animal Models

Once optimized in vitro, the probe are used and demonstrated for their efficacy in identifying prostate cancer in rat models. Adult male Copenhagen rats (5-6 weeks old, 200-300 grams) were used. Dunning R 3327 AT3.1 rat prostate carcinoma cell line are used to grow tumors in Copenhagen rats. The cells are cultured in a culture medium consisting of DMEM supplemented with 10% FBS. After culturing, the cells were injected, with 1 million cells ($1\times10^6$) in 0.1 ml of media, subcutaneously in the skin pedicles in the foreback of Copenhagen rats. After the injection, the time required for the tumor to grow is approximately 7 to 10 days.

Once the rat prostate tumors reach 0.5-1 cm in diameter, the present inventors started taking tri-modal spectroscopic measurements with the newly developed system for light scattering, autofluorescence lifetime, and diffuse NIR reflectance. The rat are under general anesthesia by inhaling 3% isoflurane in air at a flow rate of 1 dm$^3$/min during the optical readings, and the probe was placed on the skin of the tumor for data collection. The measurements were repeated at multiple sites on the tumor and a chosen area of muscle for comparison. Such measurements are continued for a few days, followed by open-skin measurements before sacrificing the animal. During the open-skin measurement, the rat was under general anesthesia, and the tumor were exposed for the tri-modal optical readings.

Development of Classification Algorithms

Minimal Distance Method (MDM). There are two phases in using MDM: the training and classification phase. In the training phase, (1) select respective parameters from the three spectroscopic techniques, such as A's, B's, C's, as diagnostic/classification markers to differentiate prostate cancer from normal tissue; (2) based on the mean values of A's, B's, C's derived from animal and human measurements, compute the center location, P, of the parameters in the multi-dimensional A's-B's-C's space for cancer. (The mean derived values of A's, B's, and C's are the center locations.) (3) calculate the distances from all other data points to the center (of A's, B's, and C's) in the multi-dimensional space, and then compute the standard deviation, $\sigma$, for the distances from all data points to the center. (4) This standard deviation can be used as a threshold to classify cancer and normal tissue.

In the classification phase, the present inventors (1) first obtain the set of A's, B's, C's parameters to be identified, (2) calculate the distance, R, to the center, P point, as determined in the training phase, given above, (3) compute the normalized distance as $R_N=R/\sigma$ between the unknown data point and the center point, P, (4) compare $R_N$ with the pre-defined threshold given in the training phase, and to classify the tissue.

Support Vectors Machine (SVM)

Mathematically, the classification function in SVM can be written as $f(x,\alpha)=\Sigma y_i \alpha_i K(x_i,x)+b$ where $\alpha_i$, b are model parameters and K is a kernel function. Given a set of N clinical data, which composed of input X (such as A's, B's, and C's) and output Y (−1 for normal tissue, +1 for cancer tissue), the parameters in the SVM are calculated to minimize the error from the SVM output and the known data while maximizing the margin between the two classes. This process is known as the training of SVM.

Once SVM is trained, it can be used to perform prediction. Given a set of measured parameters (x), the SVM classification is achieved by the following calculation: $Y(x)=\text{sign}(f(x,\alpha))$. Note that Y−1 for normal tissue, Y=+1 for cancer tissue. While there are many classification schemes in the literature, SVM is chosen for this research for the following reasons: (1) SVM has a strong theoretical background, (2) SVM can be applied to large data set, (3) SVM algorithm is flexible, (4) SVM is very accurate and (5) SVM can be implemented in a silicon chip. The flexibility of SVM stems from the variety of choices of kernel functions, such as linear, polynomial, radial basis function (RBF) and Sigmoid function. Gaussian RBF is used in this research:

Gaussian: Radial Basis function (RBF): $K(x_i,x_j)=\exp(-\gamma\|x_i-x_j\|^2)$, $\gamma>0$.

Computationally, the training of SVM involves the solution of the quadratic programming (QP) problem:

$$\text{Minimize } \frac{1}{2}\sum_{i=1}^{N}\sum_{j=1}^{N} y_i y_j \alpha_i \alpha_j \left(K(x_i,x_j)+\frac{1}{C}\delta_{ij}\right) - \sum_{i=1}^{N} \alpha_i \quad (6)$$

$$\text{Such that } \sum_{i=1}^{N} \alpha_i y_i = 0, \alpha_i \geq 0, i=1,\ldots,N$$

The support vector output is $$f(x)=\sum_{i=1}^{N} y_i \alpha_i K(x_i,x)+b.$$

The present inventors used the MATLAB quadprog function to solve the QP problem and implemented a developed smoothed support vector machine (SSVM) in which the training involves the solution of an unconstrained problem only. SSVM has the same accuracy as SVM but is much faster to train. This makes SSVM a good candidate for real-time implementation. It should be noted that SVM could be used for multidimensional binary classification. SVM has also been extended for multiclass classification.

Human Prostate Measurements

Human measurements in the operating room were conducted using the newly developed tri-modal spectroscopic system, the laparoscopic NIR probe, and the classification algorithms to demonstrate the ability of the tri-modal technique for identification of prostate adenocarcinoma during laparoscopic prostatectomy.

The newly constructed and animal validated probe were used during human laparoscopic radical prostatectomy (n=12). During the surgery, by the time when the human prostate gland is just completely resected, the probe was inserted through the laparoscopic ports and rested on the resected gland. Three different optical spectra (light scattering reflectance, autofluorescence lifetime, and diffuse NIR reflectance were recorded and stored for later analysis. Several landmarks were selected for the measurement sites: the tip of Apex, four quarters of posterior and anterior of the prostate. Several spectra per modality were taken in each data-collection site with a few millimeters apart.

The optical spectra were subjected to the classification program. Success are defined as having a greater than 90% rate of correct tissue identification. Should one not be able to correctly identify prostate adenocarcinoma, the observed trimodal optical spectra are subjected to re-analysis by the mathematical modeling algorithms to develop an updated classification scheme specific for human prostate tissues. Following this adjustment the probe are tested on another 15 human patients. Multiple readings were obtained (n=5) and tested in humans to determine reproducibility. Correct tissue identification at a 90% rate are the acceptable limit for the probes.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An optical spectroscopy system to differentiate malignant tumors from benign tumors of one or more tissues comprising:
    at least one electromagnetic radiation source for illuminating one or more tissues;
    an intraoperative optical probe connected to the electromagnetic radiation source and adapted to contact the one or more tissues and adapted to transmit electromagnetic radiation from the electromagnetic radiation source to illuminate the one or more tissues and adapted to relay a light-scattering reflectance, a time-resolved auto-fluorescence and a diffuse near infrared emission;
    a detector connected to the intraoperative optical probe and adapted to capture and receive the light-scattering reflectance, time-resolved auto-fluorescence and diffuse near infrared emission from the one or more tissues; and
    a computer device connected with the detector, wherein the computer device comprises one or more tissue classification algorithms comprising minimal distance method and support vector machine algorithm that differentiate a malignant tumor from a benign tumor.

2. The system of claim 1, further comprising one or more displays to display projections of the light-scattering reflectance, time-resolved auto-fluorescence and diffuse near infrared emission from the illuminated one or more tissues and display results of tissue classification from the computer device.

3. The system of claim 1, wherein the intraoperative optical probe comprises a cystoscope, ureterscope, or a fiber optic endoscope.

4. The system of claim 1, wherein the intraoperative optical probe is a fiber optic bundle comprising:
    at least nine individual fibers, wherein at least one of the individual fibers transmits white light from the electromagnetic radiation source;
    at least one of the individual fibers connected to the detector used for measuring light-scattering reflectance;
    at least one of the individual fibers used for measuring time-resolves autofluorescence; and
    at least one of the individual fibers used for measuring diffuse near-infrared reflectance.

5. The system of claim 1, wherein the one or more tissue classification algorithms comprise algorithms that determine one or more physiological parameters a few millimeters below a surface of the one or more tissues using equation:

$$R_p(\lambda) = \frac{\mu_s'(\lambda)}{k_1 + k_2 \mu_a(\lambda)}$$

where $R_p(\lambda)$ is the measured optical signal with an optical probe, $\mu_s'(\lambda)$ is the reduced scattering coefficient, $\mu_a(\lambda)$ is the absorption coefficient, and $k_1$ and $k_2$ are two calibration parameters depending only on the geometrical characteristics of the optical probes and the optical spectroscopic system.

6. The system of claim 1, wherein the one or more tissue classification algorithms determine one or more physiological parameters of the one or more tissues within one millimeter from a surface of the one or more tissues using equation:

$$\mu'_s(\lambda) = \left(1 - \frac{d_0^{1/2}}{d_s^{1/2}} \frac{\lambda - \lambda_{min}}{\lambda_{max} - \lambda_{min}}\right) \mu'_s(\lambda_{min})$$

where $\mu_s'$ is the spectral dependence of light scattering, $d_o$ and $d_s$ are effective scatter factors and $\lambda_{min}$ and $\lambda_{max}$ define the range of wavelengths where reflectance measurements are performed.

7. The system of claim 1, wherein the one or more tissues comprise a normal tissue, a malignant tumor, a benign tumor or any combinations thereof.

8. The system of claim 7, wherein the malignant or the benign tumor comprises a kidney or a prostate tumor.

9. A method for differentiating malignant tumors from benign tumors of one or more tissues comprising the steps of:
   providing the optical spectroscopy system of claim 1;
   contacting the one or more tissues with an intraoperative optical probe connected to an electromagnetic radiation source of the optical spectroscopy system;
   interrogating the one or more tissues with a directed electromagnetic radiation from the electromagnetic radiation source having a light-scattering reflectance, a time-resolved auto-fluorescence and a diffuse near infrared emission;
   detecting the light-scattering reflectance, the time-resolved auto-fluorescence and the diffuse near infrared emission from the one or more tissues using a detector;
   performing one or more computational operations on the detected light-scattering reflectance, time-resolved auto-fluorescence and diffuse near infrared emissions to obtain data; and
   analyzing the data to determine the physiological parameters of the one or more tissues.

10. The method of claim 9, wherein the one or more tissues comprise normal tissue, a malignant tumor, a benign tumor or any combinations thereof.

11. The method of claim 10, wherein the malignant or the benign tumor comprises a kidney or a prostate tumor.

12. The method of claim 9, wherein the step of performing one or more computation operations comprises performing calculations to determine physiological parameters a few millimeters below a surface of the one or more tissues using the equation:

$$R_p(\lambda) = \frac{\mu'_s(\lambda)}{k_1 + k_2 \mu_a(\lambda)}$$

where $R_p(\lambda)$ is the measured optical signal with an optical probe, $\mu_s'(\lambda)$ is the reduced scattering coefficient, $\mu_a(\lambda)$ is the absorption coefficient, and $k_1$ and $k_2$ are two calibration parameters depending only on the geometrical characteristics of the optical probes and the optical spectroscopic system.

13. The method of claim 9, wherein the step of performing one or more computation operations comprises performing calculations to determine physiological parameters of the one or more tissues within one millimeter from a surface of the one or more tissues using the equation:

$$\mu'_s(\lambda) = \left(1 - \frac{d_0^{1/2}}{d_s^{1/2}} \frac{\lambda - \lambda_{min}}{\lambda_{max} - \lambda_{min}}\right) \mu'_s(\lambda_{min})$$

where $\mu_s'$ is the spectral dependence of light scattering, $d_o$ and $d_s$ are effective scatter factors and $\lambda_{min}$ $\lambda_{max}$ define the range of wavelengths where reflectance measurements are performed.

14. The method of claim 9, wherein the step of performing one or more computation operations comprise calculations using minimal distance method and support vector machine algorithm.

* * * * *